(12) United States Patent
Rossomando et al.

(10) Patent No.: US 8,263,553 B2
(45) Date of Patent: Sep. 11, 2012

(54) NEUBLASTIN VARIANTS

(75) Inventors: Anthony Rossomando, South Grafton, MA (US); Laura Silvian, Waban, MA (US); R. Blake Pepinsky, Arlington, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1324 days.

(21) Appl. No.: 11/573,773

(22) PCT Filed: Aug. 18, 2005

(86) PCT No.: PCT/US2005/029637
§ 371 (c)(1),
(2), (4) Date: Jul. 24, 2007

(87) PCT Pub. No.: WO2006/023781
PCT Pub. Date: Mar. 2, 2006

(65) Prior Publication Data
US 2008/0039385 A1 Feb. 14, 2008

Related U.S. Application Data

(60) Provisional application No. 60/602,825, filed on Aug. 19, 2004, provisional application No. 60/694,067, filed on Jun. 24, 2005.

(51) Int. Cl.
*A61K 38/18* (2006.01)
*C07K 1/00* (2006.01)
*C07H 21/04* (2006.01)

(52) U.S. Cl. ............ 514/8.3; 435/69.7; 435/320.1; 435/325; 536/23.5; 530/324; 530/350

(58) Field of Classification Search .......... None
See application file for complete search history.

(56) References Cited

U.S. PATENT DOCUMENTS

| | | |
|---|---|---|
| 4,352,883 A | 10/1982 | Lim |
| 4,353,888 A | 10/1982 | Sefton |
| 4,407,957 A | 10/1983 | Lim |
| 4,883,666 A | 11/1989 | Sabel et al. |
| 4,968,733 A | 11/1990 | Muller et al. |
| 4,976,859 A | 12/1990 | Wechs |
| 5,084,350 A | 1/1992 | Chang et al. |
| 5,158,881 A | 10/1992 | Aebischer et al. |
| 5,194,596 A | 3/1993 | Tischer et al. |
| 5,284,761 A | 2/1994 | Aebischer et al. |
| 5,350,836 A | 9/1994 | Kopchick et al. |
| 5,414,135 A | 5/1995 | Snow et al. |
| 5,445,934 A | 8/1995 | Fodor et al. |
| 5,496,804 A | 3/1996 | Reed et al. |
| 5,525,464 A | 6/1996 | Drmanac et al. |
| 5,618,531 A | 4/1997 | Cherksey |
| 5,641,749 A | 6/1997 | Yan et al. |
| 5,650,494 A | 7/1997 | Cerletti et al. |
| 5,654,007 A | 8/1997 | Johnson et al. |
| 5,733,729 A | 3/1998 | Lipshutz et al. |
| 5,754,524 A | 5/1998 | Wark |
| 5,770,577 A | 6/1998 | Kinstler et al. |
| 5,775,320 A | 7/1998 | Patton et al. |
| 5,780,014 A | 7/1998 | Eljamal et al. |
| 5,780,019 A | 7/1998 | Klier et al. |
| 5,785,049 A | 7/1998 | Smith et al. |
| 5,795,716 A | 8/1998 | Chee et al. |
| 5,798,113 A | 8/1998 | Dionne et al. |
| 5,800,992 A | 9/1998 | Fodor et al. |
| 5,814,607 A | 9/1998 | Patton |
| 5,834,029 A | 11/1998 | Bellamkonda et al. |
| 5,846,935 A | 12/1998 | Panayotatos |
| 5,916,555 A | 6/1999 | Lee et al. |
| 5,939,524 A | 8/1999 | Bowditch et al. |
| 6,063,757 A | 5/2000 | Urso |
| 6,083,725 A | 7/2000 | Selden et al. |
| 6,084,076 A | 7/2000 | Ejima et al. |
| 6,284,540 B1 | 9/2001 | Milbrandt et al. |
| 6,299,895 B1 | 10/2001 | Hammang et al. |
| 6,361,771 B1 | 3/2002 | Tao et al. |
| 6,593,133 B1 | 7/2003 | Johansen et al. |
| 6,677,135 B1 | 1/2004 | Sanicola-Nadel et al. |
| 6,723,344 B2 | 4/2004 | Sakiyama-Elbert et al. |
| 6,734,284 B1 | 5/2004 | Johansen et al. |
| 7,067,473 B1 | 6/2006 | Masure |
| 7,115,257 B1 | 10/2006 | Tao et al. |
| 7,276,580 B2 | 10/2007 | Sah et al. |
| 7,358,228 B2 | 4/2008 | Sah et al. |
| 7,442,370 B2 | 10/2008 | Sah et al. |
| 7,598,059 B2 | 10/2009 | Pederson et al. |

(Continued)

FOREIGN PATENT DOCUMENTS

EP    1 373 503    11/2007

(Continued)

OTHER PUBLICATIONS

Vickers. A vaccine against Alzheimer's disease: developments to date. Drugs Aging 2002; 19(7):487-94.*
Purves, Dale, et al (Eds.), Neuroscience, 2001, Sinauer Associates, Inc., 2nd Edition, pp. 75, 367, 400, 403, 554, 555, and 678.*
Stokes et al. Experimental modeling of human spinal cord injury: a model that crosses the species barrier and mimic the spectrum of human cytopathology, Spinal Cord 40: 101-109, 2002.*
Talac et al. Animal models of spinal cord injury for evaluation of tissue engineering treatment strategies, Biomaterials 25: 1505-1510, 2004.*
Mills et al. Strain and model differences in behavioral outcomes after spinal cord injury in rat, J. Neurotrauma Aug;18(8):743-56, 2001.*

(Continued)

*Primary Examiner* — Daniel E Kolker
*Assistant Examiner* — Gregory S Emch
(74) *Attorney, Agent, or Firm* — Fish & Richardson P.C.

(57) ABSTRACT

Compositions and methods for folding proteins belonging to the transforming growth factor beta superfamily are disclosed. The compositions and methods allow for the folding of such proteins when produced in an expression system that does not yield a properly folded, biologically active product.

219 Claims, 11 Drawing Sheets

U.S. PATENT DOCUMENTS

| | | | |
|---|---|---|---|
| 7,601,518 B2 | 10/2009 | Wahlberg et al. |
| 7,655,463 B2 | 2/2010 | Sah et al. |
| 2002/0002269 A1 | 1/2002 | Milbrandt et al. |
| 2002/0055467 A1 | 5/2002 | Johansen et al. |
| 2002/0114780 A1 | 8/2002 | Bankiewicz et al. |
| 2003/0078373 A1 | 4/2003 | Fersht et al. |
| 2003/0100497 A1 | 5/2003 | Baker et al. |
| 2003/0166537 A1 | 9/2003 | Hanke |
| 2003/0186267 A1 | 10/2003 | Feder et al. |
| 2004/0028613 A1 | 2/2004 | Quay |
| 2004/0077543 A1 | 4/2004 | Sah et al. |
| 2004/0142418 A1 | 7/2004 | Sah et al. |
| 2004/0230043 A1 | 11/2004 | Johansen et al. |
| 2004/0242472 A1 | 12/2004 | Shelton et al. |
| 2004/0265972 A1 | 12/2004 | Weintraub et al. |
| 2005/0069520 A1 | 3/2005 | Shi et al. |
| 2005/0089960 A1 | 4/2005 | Wahlberg et al. |
| 2005/0118157 A1 | 6/2005 | McMahon et al. |
| 2005/0142098 A1 | 6/2005 | Sah et al. |
| 2005/0158824 A1 | 7/2005 | Pedersen et al. |
| 2005/0180957 A1 | 8/2005 | Scharp et al. |
| 2005/0181991 A1 | 8/2005 | Shelton et al. |
| 2005/0233359 A1 | 10/2005 | Masure et al. |
| 2006/0009625 A1 | 1/2006 | Bedows et al. |
| 2006/0014288 A1 | 1/2006 | Kim et al. |
| 2006/0122135 A1 | 6/2006 | Geerts et al. |
| 2007/0238650 A1 | 10/2007 | Sah et al. |
| 2007/0254842 A1 | 11/2007 | Bankiewicz |
| 2008/0039385 A1 | 2/2008 | Rossomando et al. |
| 2008/0227703 A1 | 9/2008 | Johansen et al. |
| 2008/0249287 A1 | 10/2008 | Rossomando et al. |
| 2008/0260702 A1 | 10/2008 | Jorgensen |
| 2008/0306212 A1 | 12/2008 | Sah et al. |
| 2009/0221495 A1 | 9/2009 | Rossomando et al. |
| 2009/0258831 A1 | 10/2009 | Sah |
| 2010/0056440 A1 | 3/2010 | Rossomando et al. |
| 2010/0234293 A1 | 9/2010 | Johansen et al. |
| 2010/0261654 A1 | 10/2010 | Rossomando et al. |
| 2010/0292142 A1 | 11/2010 | Sah et al. |

FOREIGN PATENT DOCUMENTS

| | | |
|---|---|---|
| EP | 1 930 439 | 6/2008 |
| JP | 11-310600 | 11/1999 |
| JP | 2002-534957 | 10/2002 |
| JP | 2003-310258 | 11/2003 |
| RU | 2225728 | 8/1999 |
| WO | WO 92/19195 | 11/1992 |
| WO | WO 93/06116 | 4/1993 |
| WO | WO 95/05452 | 2/1995 |
| WO | WO 97/08196 | 3/1997 |
| WO | WO 97/11964 | 4/1997 |
| WO | 97/19693 | 6/1997 |
| WO | WO 98/32869 | 7/1998 |
| WO | WO 99/03887 | 1/1999 |
| WO | WO 99/13090 | 3/1999 |
| WO | WO 99/42486 | 8/1999 |
| WO | WO 99/43813 | 9/1999 |
| WO | WO 99/49039 | 9/1999 |
| WO | WO 00/01815 | 1/2000 |
| WO | WO 00/04050 | 1/2000 |
| WO | 00/15665 | 3/2000 |
| WO | WO 00/18799 | 4/2000 |
| WO | WO 00/34475 | 6/2000 |
| WO | WO 00/73348 | 12/2000 |
| WO | WO 01/47946 | 7/2001 |
| WO | WO 01/53486 | 7/2001 |
| WO | WO 01/66164 | 9/2001 |
| WO | WO 01/76639 | 10/2001 |
| WO | 01/87925 | 11/2001 |
| WO | WO 02/46430 | 6/2002 |
| WO | WO 02/051433 | 7/2002 |
| WO | WO 02/060929 | 8/2002 |
| WO | WO 02/072826 | 9/2002 |
| WO | WO 02/078730 | 10/2002 |
| WO | 03/044055 | 5/2003 |
| WO | WO 2004/002763 | 1/2004 |
| WO | WO 2004/069176 | 8/2004 |
| WO | WO 2004/094592 | 11/2004 |
| WO | WO 2004/108760 | 12/2004 |
| WO | WO 2005/039643 | 5/2005 |
| WO | WO 2006/023781 | 3/2006 |
| WO | WO 2006/023782 | 3/2006 |
| WO | WO 2007/042040 | 4/2007 |
| WO | WO 2007/100898 | 9/2007 |
| WO | WO 2007/103182 | 9/2007 |
| WO | WO 2008/137574 | 11/2008 |
| WO | WO 2009/020964 | 2/2009 |

OTHER PUBLICATIONS

Abrams et al., "Emerging strategies to promote improved functional outcome after peripheral nerve injury," Restor. Neurol. Neurosci., 23(5-6):367-82 (2005).

Aebischer et al, "Recombinant proteins for neurodegenerative diseases: the delivery issue," Trends in Neuroscience, Elsevier, Amsterdam, NL 24(9):533-540 (2001).

Aebischer et al., "Intrathecal delivery of CNTF using encapsulated genetically modified xenogeneic cells in amyotrophic lateral sclerosis patients," Nature Medicine, 2:696-699 (1996).

Airaksmen et al., GDNF family neurotrophic factor signaling: four masters, one servant, Mol. Cell Neurosci., 13:313-325 (1999).

Alfano et al., "The major determinant of the heparin binding of glial cell-line-derived neurotrophic factor is near the N-terminus and is dispensable for receptor binding," Biochem. J., 404(1):131-40 (2007).

Algvere et al., "Transplantation of RPE in age-related macular degeneration: observations in disciform lesions and dry RPE atrophy," Graefe's Arch. Clin. Exp. Ophthalmol., 235:149-158 (1997).

Anderson, "Human gene therapy," Nature, 392:25-30 (1998).

Andres et al., "Multiple effects of artemin on sympathetic neurone generation, survival and growth," Development 128:3685-3695 (2001).

Anonymous, "Anti-human Artemin Antibody," R&D Systems Product Data Sheets (Dec. 27, 2006), [online] XP002505114. Retrieved from the Internet: http://www.rndsystems.com/pdf/AF2589.pdf [retrieved on Nov. 21, 2008].

Anonymous, "Monoclonal Anti-human Artemin Antibody," R&D Systems Product Data Sheets (Mar. 23, 2006), [online] XP002505115. Retrieved from the Internet: http://www.rndsystems.com/pdf/MAB2589.pdf [retrieved on Nov. 21, 2008].

Atschul et al., "Gapped BLAST and PSI-BLAST: a new generation of protein database search programs," Nucl. Acids Res., 25:3389-3402 (1997).

Baloh et al. "Artemin, a novel member of the GDNF ligand family, supports peripheral and central neurons and signals through the GFRalpha3-RET receptor complex," Neuron, 21(6):1291-1302 (1998).

Baloh et al., "Functional mapping of receptor specificity domains of glial cell line-derived neurothropic factor (GDNF) family ligands and production of GFR alpha 1 RET-specific agonists," J. of Biological Chemistry, 275(5):3412-3420 (2000).

Baudet et al., "Positive and negative interactions of GDNF, NTN and ART in developing sensory neuron subpopulations, and their collaboration with neurotrophins," Development, 127:4335-4344 (2000).

Bauskin et al., "The propeptide of macrophage inhibitory cytokine (MIC-1), a TGF-β superfamily member, acts as a quality control determinant for correctly folded MIC-1," The EMBO Journal, 19(10):2212-2220 (2000).

Bendtsen et al., "Improved prediction of signal peptides—SignalP 3.0," J. Mol. Biol., 340(4):783-795 (2004).

Bennett et al., "Artemin has potent neurotrophic actions on injured C-fibres," J. Peripher. Nerv. Syst., 11(4):330-45 (2006).

Bonde et al., "GDNF and neublastin protect against NMDA-induced excitotoxicity in hipocampal slice cultures," Neuroreport., 11:4069-4073 (2000).

Bootcov et al., "MIC-1, a novel macrophage inhibitory cytokine, is a divergent member of the TGF-β superfamily," Pro. Natl. Acad. Sci. U.S.A., 94:11514-11519 (1997).

Bork, "Go hunting in sequence databases but watch out of the traps," Trends in Genetics, 12:425-427 (1996).

Bork, "Powers and Pitfalls in Sequence analysis: the 70% Hurdle," Genome Research, 10:398-400 (2000).
Borodovsky et al., "Detection of new genes in a bacterial genome using Markov models for three gene classes," Nucl. Acids Res., 23:3554-3562 (1995).
Boucher et al "Artemin prevents injury-induced changes in small sensory neurons," Abstracts of the Society for Neuroscience, Society for Neuroscience, Washington D.C. 26(1/2):63305 (2000).
Brenner, "Errors in genome annotation," Trends in Genetics, 15:132-133 (1999).
Burgess et al., "Possible dissociation of the heparin-binding and mitogenic activities of heparin-binding (acidic fibroblast) growth factor-1 from its receptor-binding activities by site-directed mutagenesis of a single lysine residue," J. of Cell Biology, 111:2129-2138 (1990).
Callister et al., Soc. for Neuroscience Abstracts 27(1):36.11 (2001).
Campbell et al., "Mechanisms of Neuropathic Pain," Neuron, 52:77-92 (2006).
Carmillo et al., "Glial Cell Line-Derived Neurotrophic Factor (GDNF) Receptor α-1(GFRα1) is Highly Selective for GDNF versus Artemin," Biochemistry, 44:2545-2554 (2005).
Ceyhan et al., "The neurotrophic factor artemin promotes pancreatic cancer invasion," Ann. Surg., 244:274-81 (2006).
Ceyhan et al., "The neurotrophic factor artemin influences the extent of neural damage and growth in chronic pancreatitis," Gut., 56(4):534-44 (2007).
Damon et al., "Vascular-derived artemin: a determinant of vascular sympathetic innervation?," Am. J. Physiol. Heart Circ. Physiol., 293:H266-H273 (2007).
Daopin et al., "Crystal structure of TGF-β2 refined at 1.8 A resolution," Proteins, 17:176-192 (1993).
Delgado et al., "The uses and properties of PEG-Linked proteins," Critical Reviews in Therapeutic Drug Carrier Systems, 9(3/4):249-304 (1992).
Doerks et al., "Protein annotation: detective work for function prediction," Trends in Genetics, 14:248-250 (1998).
During et al., "Towards gene therapy for the central nervous system," Mol. Med., 11:485-493 (1998).
Eigenbrot et al., "X-ray structure of glial cell-derived neurotrophic factor at 1 9 A resolution and implications for receptor binding," Nat. Struct. Biol., 4:435-438 (1997).
Enomoto et al., "RET signaling is essential for migration, axonal growth and axon guidance of developing sympathetic neurons," Development, 128:3963-3974 (2001).
Enzmann et al., "Immunological problems of transplantation into the subretinal space," Acta Anat., 162:178-183 (1998).
Fairlie et al., "The propeptide of the transforming growth factor-β superfamily member, macrophage inhibitory cytokine-1 (MIC-1), is a multifunctional domain that can facilitate protein folding and secretion," J. of Biol. Chem., 276(20):16911-16918 (2001).
Finsen et al., "Somatostatin and neuropeptide Y in organotypic slice cultures of the rat hippocampus: an immunocytochemical and in situ hybridization study," Neurosci., 47:105-113 (1992).
Fjord-Larsen, et al. "Efficient in vivo protection of nigral dopaminergic neurons by lentiviral gene transfer of a modified Neurturin construct," Experimental Neurology, 195:49-60 (2005).
Flanders et al., "TGFβ," Laboratory of Cell Regulation and Carcinogenesis, National Cancer Institute, 719-746, 2000.
Francis et al., "Pegylation of Cytokines and other therapeutic proteins and peptides: the importance of biological optimization of coupling techniques," Int'l. Journal of Hematology, Elsevier Science Publishers, NL., 68(1):1-18 (1998).
Friedmann, "Principles for human gene therapy studies," Science, 287:2163-2164 (2000).
Gardell et al., "Multiple actions of systemic artemin in experimental neuropathy," Nat Med., 9(11):1383-89 (2003).
GenBank Accession No. AA844072, 2 pages (1998).
GenBank Accession No. AC005037, Waterston, 54 pages (1998).
GenBank Accession No. AC005038, Sulston et al., 96 pages (2001).
GenBank Accession No. AC005051, Waterston, 38 pages (1998).
GenBank Accession No. AF040962, Milbrandt et al., 2 pages (1998).
Genbank Accession No. AF120274, Rosenblad et al., 3 pages (1999).
Gilchuk, "Assessment of renaturation methods for industrial producing recombinant proteins in biologically active form from E.coli inclusion bodies," Biopolymers and Cell, 20(3):182-192 (2004).
Griffin et al., "Assessment of cutaneous innervation by skin biopsies," Current Opinion in Neurology, 14:655-659 (2001).
Guerra et al., "PEGylation prevents the N-terminal degradation of megakaryocyte growth and development factor," Pharm. Res., 15(12):1822-1827 (1998).
Gustafsson, "New insights in oestrogen receptor (ER) research—the ERbeta," Eur. J. Cancer, 36 Suppl. 4:S16 (2000).
Hall et al., "Eukaryotic and Prokaryotic Signal Peptides Direct Secretion of a Bacterial Endoglucanase by Mammalian Cells," Journal of Biological Chemistry, 265(32):19996-19999 (1990).
Hallböök et al., "Expression of Neurotrophins and Trk Receptors in the Avian Retina," J. Compar. Neurol., 364:664-676 (1996).
Hamilton et al., "Heparin coinfusion during convection-enhanced delivery (CED) increases the distribution of the glial-derived neurotrophic factor (GDNF) ligand family in rat striatum and enhances the pharmacological activity of neurturin," Experimental Neurology, 168:155-161 (2001).
Hoane et al. "Mammalian-Cell-Produced Neurturin (NTN) is More Potent Than Purified Escherichia coli-Produced NTN," Exp. Neurol., 162:189-193 (2000).
Israel et al., "Acetylcholine Release and the Cholinergic Genomic Locus," Molecular Neurobio., 16(1):1-20 (1998).
Johansen et al., "Biosynthesis of peptide precursors and protease inhibitors using new consititutive and inducible eukaryotic expression vectors," FEBS Lett., 267:289-294 (1990).
Kim et al., "An experimental model for peripheral neuropathy produced by segmental spinal nerve ligation in the rat," Pain, 50:355-363 (1992).
Kirsch et al. "Expression of ciliary neurotrophic factor receptor mRNA and protein in the early postnatal and adult rat nervous system," Neurosci. Lett., 180:163-166 (1994).
Kotzbauer et al., "Neurturin, a relative of glial-cell-line-derived neurotrophic factor," Nature, 384:467-70 (1996).
Kron et al., "Coronary revascularization rather than cardiac transplantation for chronic ischemic cardiomyopathy," Ann. Surg., 210:348-352 (1989).
Lapchak et al., "Pharmacological characterization of glial cell line-derived neurotrophic factor (GDNF): implications for GDNF as a therapeutic molecule for treating neurodegenerative diseases," Cell Tissue Res., 286:179-189 (1996).
Lapchak, "Therapeutic potential for glial cell line-derived neurotropic factor (GDNF) based upon pharmacological activities in the CNS," Rev. Neurosci., 7:165-176 (1977).
Lavail et al., "Protection of mouse photoreceptors by survival factors in retinal degenerations," Invest. Ophthalmol. Vis. Sci., 39(3):592-602 (1998).
Lee et al., "Proliferin Secreted by Cultured Cells Binds to Mannose 6-Phosphate", J. Biol. Chem., 263(7):3521-3527 (1988).
Lee et al., "Prolonged circulating lives of single-chain Fv proteins conjugated with polyethylene glycol: a comparison of conjugation chemistries and compounds," Bioconjug. Chem., 10:973-981 (1999).
Li et al., "Beta-Endorphin omission analogs: dissociation of immunoreactivity from other biological activities," PNAS, 77(6):3211-14 (1990).
Li et al., "Expression, purification, and characterization of recombinant human neurturin secreted from the yeast Pichia pastoris," Protein Expression and Purification, 30(1):11-17 (2003).
Lin et al., "GDNF: A glial cell line-derived neurotrophic factor for midbrain dopaminergic neurons," Science, 260:1130-1132 (1993).
Little et al., "Transplantation of human fetal retinal pigment epithelium rescues photoreceptor cells from degeneration in the royal college of surgeons rat retina," Invest. Ophthalmol. Vis. Sci., 37(1):204-211 (1996).
Lorenz et al., "Heteromultimeric CLC chloride channels with novel properties," Proc. Natl. Acad. Sci USA, 93:13362-13366 (1996).
Maeda et al., "Efficient Production of Active TNF α by albumin Signal Peptide," Biochemistry and Molecular Biology International, Academic Press, London, GB, 42(4):825-832 (1997).
Massague et al., "The TGF-β family and its composite receptor," Trends Cell Biol., 4:172-178 (1994).

Mason, "The RET receptor tyrosine kinase: activation, signalling and significance in neural development and disease," Pharm. Acta. Helv., 74:261-4 (2000).

Masure et al., "Enovin, a novel member of the GDNF family of neurotrophic growth factors with growth promoting and neuroprotective effects on neuronal cells," a poster presentation from Janssen Research Foundation, "Gordon Conference" held on Jun. 6-11, 1999.

Masure, et al., "Enovin, a member of the glial cell-line-derived neurotrophic factor (GDNF) family with growth promoting activity on neuronal cells," Eur J. Biochem., 266:892-902 (1999).

Masure et al., "Mammalian GFRalpha -4, a divergent member of the GFRalpha family of coreceptors for glial cell line-derived neurotrophic factor family ligands, is a receptor for the neurotrophic factor persephin," J. Biol. Chem., 275:39427-34 (2000).

Matsushita et al., "Cloning and structural organization of the gene encoding the mouse glial cell line-derived neurotrophic factor, GDNF," Gene, 203:149-157 (1997).

McDonald et al., "A structural superfamily of growth factors containing a cystine knot motif.," Cell, 73:421-424 (1993).

Merlo et al. "The Mouse *int-2* Gene Exhibits Basic Fribroblast Growth Facctor Activity in a Basic Fibroblast Growth Factor-responsive Cell Line," Cell Growth & Differentiation, 1:463-472 (1990).

Milbrandt et al., "Persephin, a novel neurotrophic factor related to GDNF and Neurturin," Neuron, 20:245-253 (1998).

Moore et al., "Renal and neuronal abnormalities in mice lacking GDNF," Nature, 382:76-79 (1996).

Moustakas et al., "Smad regulation in TGF-β signal transduction," J. of Cell Science, 114:4359-4369 (2001).

Ngo et al., "The Protein Folding Problem and Tertiary Structure Prediction," Birkhäuser, 492-495 (1994).

Nielsen et al., "Identification of prokaryotic and eukaryotic signal peptides and prediction of their cleavage sites," Protein Engineering, 10(1):1-6 (1997).

Nielsen et al., "Prediction of signal peptides and signal anchors by a hidden Markov model," Proceedings of the 6th International Conference on Intelligent systems for Molecular Biology, 122-130 (1998).

Nishino et al., "GFR alpha3, a component of the artemin receptor, is required for migration and survival of the superior cervical ganglion," Neuron, 23(4):725-736 (1999).

Norton et al., "Bacterial beta-Galactosidase as a Marker of Rous Sarcoma Virus Gene Expression and Replication," Mol. Cell. Biol., 5:281-290 (1985).

Orozco et al., "Nociceptive Neurons Express GFRα3," Society for Neuroscience, Abstracts 26 (1-2): Abstract No. 412.7 (2000).

Orozco et al., "GFRalpha3 is expressed predominantly in nociceptive sensory neurons," Eur. J. Neurosci., 13(11):2177-82 (2001).

Palmiter, "Heterologous introns can enhance expression of transgenes in mice," PNAS, 88:478-482 (1991).

Park et al., "Coordinated interaction of the vascular and nervous systems: from molecule- to cell-based approaches," Biochem. Biophys. Res. Commun., 311:247-253 (311) (2003).

Pawson et al., "Assembly of cell regulatory systems through protein interaction domains," Science, 300:445-452 (2003).

PIR_80 Accession No. 14968, Aug. 2, 1996.

Rakowicz et al., "Glial Cell Line-Derived Neurotrophic Factor Promotes the Survival of Early Postnatal Spinal Motor Neurons in the Lateral and Medial Motor Columns in Slice Culture," The Journal of Neuroscience, 22(10):3953-3962 (2002).

Rattenholl et al., "Pro-sequence assisted folding and disulfide bond formation of human nerve growth factor," J. Mol. Biol., 305:523-533 (2001).

Rattenholl et al., "The pro-sequence facilitates folding of human nerve growth factor from *Escherichia coli* inclusion bodies," Eur. J. Biochem., 268:3296-3303 (2001).

Reddy, "Controlled-release peylation, liposomal formulations: new mechanisms in the delivery of injectable drugs," Annals of Pharmacotherapy, 34(7/8):915-923 (2000).

Reinshagen et al., "Commercial recombinant human β-Nerve Growth factor and adult rat dorsal root ganglia contain an identical molecular species of nerve growth factor prohormone," J. of Neurochemistry, 74:2127-2133 (2000).

Riganti et al., "Nitroarginine methyl ester and canavanine lower intracellular reduced glutathione," Free Radic. Biol. Med., 35(10):1210-6 (2003).

Robertson et al., "The GDNF-RET signaling in partnership," Trends Genet., 13:1-3 (1997).

Rosenberg et al., "Gene therapist, heal thyself," Science, 287:1751 (2000).

Rosenberg et al., "Vectors for selective expression of cloned DNAs by T7 RNA polymerase," Gene, 56:125-135 (1987).

Rosenblad et al., "In vivo protection of nigral dopamine neurons by lentiviral gene transfer of the novel GDNF-family member neublastin/artemin," Molecular and Cellular Neuroscience, 15(2):199-214 (2000).

Rosenblad et al., "In vivo protection of nigral dopamine neurons by lentiviral gene transfer of the novel GDNF-family member neublastin/artemin," Mol. Cell Neurosci., 18(3):332-333 (2001).

Saarma et al., "Other neurotrophic factors: glial cell line-derived neurotrophic factor (GDNF)," Microsc. Res. Tech., 45(4-5):292-302 (1999).

Saarma, "GDNF: A stranger in the TGF-beta superfamily?" European Journal of Biochemistry, 267(24):6968-6971 (2000).

Sadick et al., "Analysis of heregulin-induced ErbB2 phosphorylation with a high-throughput Kinase receptor activation enzyme-linked immunosorbant assay," Anal. Biochem., 235(2):207-14 (1996).

Sah et al., "Prevention and Reversal of Experimental Neuropathic Pain by Systemic Neublastin," Society for Neuroscience Abstracts, 27(1):361 (2001).

Sah et al., "New approaches for the treatment of pain: the GDNF family of neurotrophic growth factors," Curr. Top Med. Chem., 5(6):577-83 (2005).

Sanicola et al., "Glial cell line-derived neurotrophic factor-dependent RET activation can be mediated by two different cell-surface accessory proteins," Proc Natl Acad Sci, USA, 94:6238-6243 (1997).

Sauer et al., "Progressive degeneration of nigrostriatal dopamine neurons following intrastraiatal terminal lesions with 6-hydroxydopamine: a combined retrograde tracing and immunocytochemical study in the rat," Neuroscience, 59:401-415 (1994).

Schmidt et al. "In vivo kinetics as a sensitive method for testing physiologically intact human recombinant apolipoprotein A-1: comparison of three different expression systems," Clinica Chimica Acta, 268(1-2):41-60 (1997).

Skolnick et al. "From genes to protein structure and function: novel applications of computational approaches in the genomic era," Trends in Biotech., 18(1):34-39 (2000).

Sloot et al., "Detection of salicylate and its hydroxylated adducts 2.3- and 2.5-dihydroxybenzoic acids as possible indices for in vivo hydroxyl radical formation in combination with catechol- and indoleamines and their metabolites in cerebrospinal fluid and brain tissue," J. Neurosci. Meth., 60:141-149 (1995).

Smith et al. "The challenges of genome sequence annotation" or "The devil is in the details," Nature Biotechnology, 15:1222-1223 (1997).

Stoppini et al., "A simple method for organotypic cultures of nervous tissue," J. Neurosci. Methods, 37:173-182 (1991).

Thompson et al., "The ClustalX windows interface: flexible strategies for multiple sequence alignment aided by quality analysis tools," Nucl. Acids Res., 25:4876-4882 (1997).

Tseng et al., "Neurturin protects dopaminergic neurons following medial forebrain bundle axotomy," Mol. Neurosci, 9:1817-1822 (1998).

Unsicker, "GDNF: a cytokine at the interface of TGF-betas and neurotrophins," Cell Tissue Res., 286:175-178 (1996).

Vallejo et al., "Optimized procedure for renaturation of recombinant human bone morphogenetic protein-2 at high protein concentration," Biotechnol. Bioeng., 85(6):601-609 (2004).

Varmus, "Gene therapy: Not ready for prime time," Nature Medicine, 2(1):7-8 (1996).

Verma et al., "Gene therapy-promises, problems and prospects," Nature, 389:239-242 (1997).

Verma, "Gene therapy: beyond 2000," Mol. Ther., 6:493 (2000).

Veronese et al., "Introduction and Overview of Peptide and Protein Pegylation," Advanced Drug Delivery Reviews, 54(4):453-456 (2002).

Von Schwedler et al., "Vif is crucial for human immunodeficiency virus type 1 proviral DNA synthesis in infected cells," J. Virol., 67:4945-4955 (1993).

Vukicevic et al., "Induction of nephrogenic mesenchyme by osteogenic protein 1 (bone morphogenetic protein 7)," PNAS USA, 93:9021-9026 (1996).

Wang et al., "Single-chain Fv with manifold N-glycans as bifunctional scaffolds for immunomolecules," Protein Eng., 11(12):1277-83 (1998).

Wang et al., "Animal and cellular models of chronic pain ," Adv. Drug Delivery Rev., 55:949-965 (2003).

Wang et al., "Inhibitory effect of endostatin expressed by human liver carcinoma SMMC7721 on endothelial cell proliferation in vitro," World Journal of Gastroenterology, 8(2):253-257 (2002).

Watabe et al., "Spontaneously immortalized adult mouse Schwann cells secrete autocrine and paracrine growth-promoting activities," J. Neurosci. Res., 41:279-90 (1995).

Wefstaedt et al., "Neurotrophic factors of the GDNF family and their receptors are detectable in spiral ganglion cells of normal hearing as well as of deafened rats," Laryngorhinootologie, 85(11):802-8 (2006) (English abstract only, see p. 807).

Wells, "Additivity of Mutational Effects in Proteins," Biochemistry, 29:8509-8517 (1990).

West et al., "Estimation of the Number of Somatostatin Neurons in the Striatum: An In Situ Hybridization Study Using the Optical Fractionator Method," J. Comp. Neurol., 370:11-22 (1996).

White et al., "Chemokines: integrators of pain and inflammation," Nat Rev. Drug discovery 4:834-844 (2005).

Zufferey et al., "Multiply attenuated lentiviral vector achieves efficient gene delivery in vivo," Nat. Biotechnol., 15:871-875 (1997).

Airaksinen et al., "The GDNF family: signalling, biological functions and therapeutic value," Nature Reviews, Neuroscience 3:383-394 (May 2002).

Bennett et al., "A distinct subgroup of small DRG cells express GDNF receptor components and GDNF is protective for these neurons after nerve injury," J. Neurosci. 18(8):3059-3072 (Apr. 15, 1998).

Bennett, G., "An animal model of neuropathic pain: A review," Muscle & Nerve 16:1040-1048 (1993).

Frankel et al., "High-Level Expression and Purifcation of the Recombinant Diphtheria Fusion Toxin DTGM for PHASE I Clinical Trials," Expr Purif. 16(1):190-201, (Jun. 1999).

Freynhagen et al., "The evaluation of neuropathic components in law back pain," Current Pain & Headache Reports 13:185-190 (2009).

Machelska et al., "Breaking the pain barrier," Nature Medicine 9(11):1353-1354 (2003).

Mogyoros et al., "Strength-duration properties of sensory and motor axons in amyotrophic lateral sclerosis," Brain 121:851-859 (1998).

Park et al., "Tarnscriptional regulation of artemin is related to neurite outgrowth and actin polymerization in mature DRG neurons," Neuroscience Letters 404:61-66 (2006).

Pons et al., "Massive cortical reorganization after sensory deafferentation in adult macaques," Scient. 252(5014):1857-1860 (1991).

Ramachandran et al., "Perceptual correlates of massive cortical reorganization," Science 258(5085):1159-1160 (1992).

Ramachandran, "Behavioral and MEG correlates of neural plasticity in the adult human brain," Proceedings of the National Academy of Sciences 90:10413-10420 (1993).

Ramer et al., "Functional regeneration of sensory axons into the adult spinal cord," Nature 403:312-316 (Jan. 2000).

Rico et al., "Characterization of the immunostimulatory properties of Leishmania infantum HSP70 by fusion to the *Escherichia coli* maltose-binding protein in normal and nu/nu BALB/c mice," Infect Immun. 66:1347-352 (Jan. 1998).

Rossomando et al., "In vitro and in vivo characterization of neublastin, a nociceptive neuronal trophic factor," Abstracts of the Annual Meeting of the Society for Neuroscience, Society for Neuroscience, Washington, DC, U.S., 27(1):361 (2001) (XP001121851, ISSN: 0190-5295).

Sah et al., "Neurotrophic factors as novel therapeutics for neuropathic pain," Nature Reviews 2:460-472 (2003).

Silvian, L. et al., "Artemin crystal structure reveals insights into heparan sulfate binding," Biochemistry 45(22):6801-12 (Jun. 2006).

Snider et al., "Tackling pain at the source: new ideas about nociceptors," Neuron 20:629-632 (Apr. 1998).

Trupp et al., "Peripheral expression and biological ctivities of GDNF, a new neurotrophic factor for avian and mammalian peripheral neurons," The Journal of Cell Biology 130(1):137-148 (Jul. 1995).

Wang et al., "Persistent Restoration of sensory function by immediate or delayed systemic artemin after dorsal root injury," Nature Neurosci. 11(4):488-496 (2008).

Yan, M. et al., "Two-amino acid molecular switch in an epithelial morphogen that regulates binding to two distinct receptors," Science 290:523-527 (2000).

Accession No. AF109402 (1998).

Honma, Y. et al., "Artemin is a vascular-derived neurotrophic factor for developing sympathetic neurons," Neuron 35(2):267-282, 2002.

* cited by examiner

|   | 10 | 20 | 30 | 40 | 50 |
|---|---|---|---|---|---|
| Human Neubla... 1 | MELGLGGLST | LSHCLRPRWQ | PALWPTLAAL | ALLSSVAEAS | LGSAPRSPAP |
| Mouse Neubla... 1 | MELGLAEPTA | LSHCLRPRWQ | SAMWPTLAVL | ALLSCVTEAS | LDPMSRSPAA |
| Rat Neublastin 1 | MELGLGEPTA | LSHCLRPRWQ | PALWPTLAAL | ALLSSVTEAS | LDPMSRSPAS |
| Human Neubla... 51 | REGPPPVLAS | PAGHLPGGRT | ARWCSGRARR | PPPQPSRPAP | PPPAP----P |
| Mouse Neubla... 51 | RDGPSPVLAP | PTDHLPGGHT | AHLCSERTLR | PPPQSPQPAP | PPPGPALQSP |
| Rat Neublastin 51 | RDVPSPVLAP | PTDYLPGGHT | AHLCSERALR | PPPQSPQPAP | PPPGPALQSP |
| Human Neubla... 97 | SALPRGGRAA | RAGGPGSRAR | AAGARGCRLR | SQLVPVRALG | LGHRSDELVR |
| Mouse Neubla... 101 | PAALRGARAA | RAGTRSSRAR | TTDARGCRLR | SQLVPVSALG | LGHSSDELIR |
| Rat Neublastin 101 | PAALRGARAA | RAGTRSSRAR | ATDARGCRLR | SQLVPVSALG | LGHSSDELIR |
| Human Neubla... 147 | FRFCSGSCRR | ARSPHDLSLA | SLLGAGALRP | PPGSRPVSQP | CCRPTRYEAV |
| Mouse Neubla... 151 | FRFCSGSCRR | ARSQHDLSLA | SLLGAGALRS | PPGSRPISQP | CCRPTRYEAV |
| Rat Neublastin 151 | FRFCSGSCRR | ARSPHDLSLA | SLLGAGALRS | PPGSRPISQP | CCRPTRYEAV |
| Human Neubla... 197 | SFMDVNSTWR | TVDRLSATAC | GCLG | | |
| Mouse Neubla... 201 | SFMDVNSTWR | TVDHLSATAC | GCLG | | |
| Rat Neublastin 201 | SFMDVNSTWR | TVDHLSATAC | GCLG | | |

FIG. 1

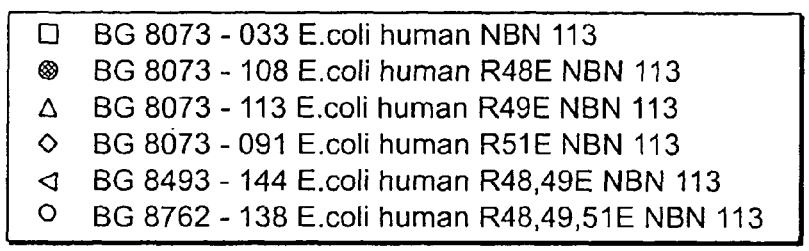
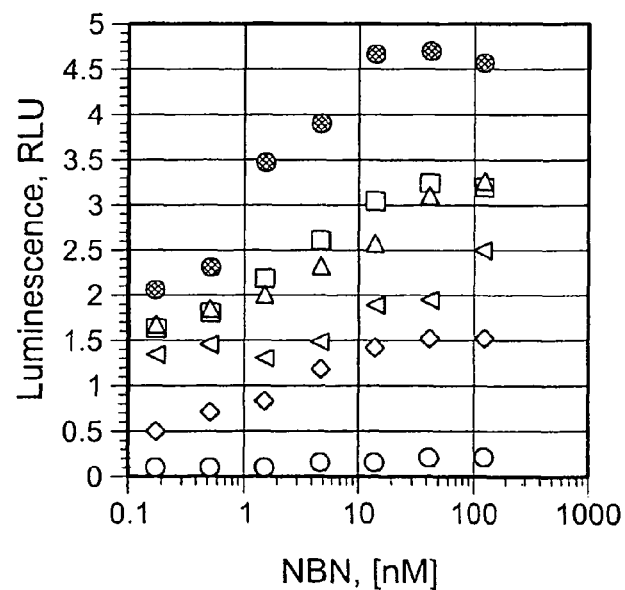
FIG. 9

SEQUENCE LISTING

<160> NUMBER OF SEQ ID NOS: 14

<210> SEQ ID NO 1
<211> LENGTH: 113
<212> TYPE: PRT
<213> ORGANISM: Homo sapiens -continued

<400> SEQUENCE: 1

Ala Gly Gly Pro Gly Ser Arg Ala Arg Ala Ala Gly Ala Arg Gly Cys
 1               5                  10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Arg Ala Arg Ser Pro His Asp Leu Ser Leu Ala Ser Leu Leu Gly Ala
    50                  55                  60

Gly Ala Leu Arg Pro Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 2
<211> LENGTH: 113
<212> TYPE: PRT
<213> ORGANISM: Artificial Sequence
<220> FEATURE:
<223> OTHER INFORMATION: Exemplary variant of human Neublastin
      polypeptide

<400> SEQUENCE: 2

Ala Gly Gly Pro Gly Ser Arg Ala Arg Ala Ala Gly Ala Arg Gly Cys
 1               5                  10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Glu
        35                  40                  45

Arg Ala Arg Ser Pro His Asp Leu Ser Leu Ala Ser Leu Leu Gly Ala
    50                  55                  60

Gly Ala Leu Arg Pro Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 3
<211> LENGTH: 113
<212> TYPE: PRT
<213> ORGANISM: Artificial Sequence
<220> FEATURE:
<223> OTHER INFORMATION: Exemplary variant of human Neublastin
      polypeptide

<400> SEQUENCE: 3

Ala Gly Gly Pro Gly Ser Arg Ala Arg Ala Ala Gly Ala Arg Gly Cys
 1               5                  10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Glu Ala Arg Ser Pro His Asp Leu Ser Leu Ala Ser Leu Leu Gly Ala

```
                    50                  55                  60
Gly Ala Leu Arg Pro Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp Arg Leu Ser Ala Thr Ala Cys Gly Cys Leu
                100                 105                 110

Gly

<210> SEQ ID NO 4
<211> LENGTH: 113
<212> TYPE: PRT
<213> ORGANISM: Artificial Sequence
<220> FEATURE:
<223> OTHER INFORMATION: Exemplary variant of human Neublastin
      polypeptide

<400> SEQUENCE: 4

Ala Gly Gly Pro Gly Ser Arg Ala Arg Ala Ala Gly Ala Arg Gly Cys
  1               5                  10                  15

Arg Leu Arg Ser Gln Leu Val Pro Val Arg Ala Leu Gly Leu Gly His
                 20                  25                  30

Arg Ser Asp Glu Leu Val Arg Phe Arg Phe Cys Ser Gly Ser Cys Arg
                 35                  40                  45

Arg Ala Glu Ser Pro His Asp Leu Ser Leu Ala Ser Leu Leu Gly Ala
 50                  55                  60

Gly Ala Leu Arg Pro Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp Arg Leu Ser Ala Thr Ala Cys Gly Cys Leu
                100                 105                 110

Gly

<210> SEQ ID NO 5
<211> LENGTH: 113
<212> TYPE: PRT
<213> ORGANISM: Artificial Sequence
<220> FEATURE:
<223> OTHER INFORMATION: Exemplary variant of human Neublastin
      polypeptide

<400> SEQUENCE: 5

Ala Gly Gly Pro Gly Ser Arg Ala Arg Ala Ala Gly Ala Arg Gly Cys
  1               5                  10                  15

Arg Leu Arg Ser Gln Leu Val Pro Val Arg Ala Leu Gly Leu Gly His
                 20                  25                  30

Arg Ser Asp Glu Leu Val Arg Phe Arg Phe Cys Ser Gly Ser Cys Glu
                 35                  40                  45

Glu Ala Arg Ser Pro His Asp Leu Ser Leu Ala Ser Leu Leu Gly Ala
 50                  55                  60

Gly Ala Leu Arg Pro Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp Arg Leu Ser Ala Thr Ala Cys Gly Cys Leu
                100                 105                 110

Gly
```

<210> SEQ ID NO 6
<211> LENGTH: 99
<212> TYPE: PRT
<213> ORGANISM: Artificial Sequence
<220> FEATURE:
<223> OTHER INFORMATION: Exemplary variant of human Neublastin
      polypeptide

<400> SEQUENCE: 6

Gly Cys Arg Leu Arg Ser Gln Leu Val Pro Val Arg Ala Leu Gly Leu
 1               5                  10                  15

Gly His Arg Ser Asp Glu Leu Val Arg Phe Arg Phe Cys Ser Gly Ser
            20                  25                  30

Cys Glu Glu Ala Arg Ser Pro His Asp Leu Ser Leu Ala Ser Leu Leu
        35                  40                  45

Gly Ala Gly Ala Leu Arg Pro Pro Gly Ser Arg Pro Val Ser Gln
    50                  55                  60

Pro Cys Cys Arg Pro Thr Arg Tyr Glu Ala Val Ser Phe Met Asp Val
65                  70                  75                  80

Asn Ser Thr Trp Arg Thr Val Asp Arg Leu Ser Ala Thr Ala Cys Gly
                85                  90                  95

Cys Leu Gly

<210> SEQ ID NO 7
<211> LENGTH: 104
<212> TYPE: PRT
<213> ORGANISM: Artificial Sequence
<220> FEATURE:
<223> OTHER INFORMATION: Exemplary variant of human Neublastin
      polypeptide

<400> SEQUENCE: 7

Ala Ala Gly Ala Arg Gly Cys Arg Leu Arg Ser Gln Leu Val Pro Val
 1               5                  10                  15

Arg Ala Leu Gly Leu Gly His Arg Ser Asp Glu Leu Val Arg Phe Arg
            20                  25                  30

Phe Cys Ser Gly Ser Cys Glu Glu Ala Arg Ser Pro His Asp Leu Ser
        35                  40                  45

Leu Ala Ser Leu Leu Gly Ala Gly Ala Leu Arg Pro Pro Pro Gly Ser
    50                  55                  60

Arg Pro Val Ser Gln Pro Cys Cys Arg Pro Thr Arg Tyr Glu Ala Val
65                  70                  75                  80

Ser Phe Met Asp Val Asn Ser Thr Trp Arg Thr Val Asp Arg Leu Ser
                85                  90                  95

Ala Thr Ala Cys Gly Cys Leu Gly
                100

<210> SEQ ID NO 8
<211> LENGTH: 113
<212> TYPE: PRT
<213> ORGANISM: Artificial Sequence
<220> FEATURE:
<223> OTHER INFORMATION: Exemplary variant of human Neublastin
      polypeptide

<400> SEQUENCE: 8

Ala Gly Gly Pro Gly Ser Arg Ala Arg Ala Ala Gly Ala Arg Gly Cys
 1               5                  10                  15

Arg Leu Arg Ser Gln Leu Val Pro Val Arg Ala Leu Gly Leu Gly His
            20                  25                  30

```
Arg Ser Asp Glu Leu Val Arg Phe Arg Phe Cys Ser Gly Ser Cys Arg
        35                  40                  45

Glu Ala Glu Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
                100                 105                 110

Gly

<210> SEQ ID NO 9
<211> LENGTH: 113
<212> TYPE: PRT
<213> ORGANISM: Artificial Sequence
<220> FEATURE:
<223> OTHER INFORMATION: Exemplary variant of human Neublastin
      polypeptide

<400> SEQUENCE: 9

Ala Gly Gly Pro Gly Ser Arg Ala Arg Ala Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Glu
        35                  40                  45

Arg Ala Glu Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
                100                 105                 110

Gly

<210> SEQ ID NO 10
<211> LENGTH: 220
<212> TYPE: PRT
<213> ORGANISM: Homo sapiens

<400> SEQUENCE: 10

Met Glu Leu Gly Leu Gly Gly Leu Ser Thr Leu Ser His Cys Pro Trp
1               5                   10                  15

Pro Arg Arg Gln Pro Ala Leu Trp Pro Thr Leu Ala Ala Leu Ala Leu
            20                  25                  30

Leu Ser Ser Val Ala Glu Ala Ser Leu Gly Ser Ala Pro Arg Ser Pro
        35                  40                  45

Ala Pro Arg Glu Gly Pro Pro Val Leu Ala Ser Pro Ala Gly His Leu
    50                  55                  60

Leu Pro Gly Gly Arg Thr Ala Arg Trp Cys Ser Gly Arg Ala Arg Arg
65                  70                  75                  80

Pro Pro Pro Gln Pro Ser Arg Pro Ala Pro Pro Pro Ala Pro Pro
                85                  90                  95

Ser Ala Leu Pro Arg Gly Gly Arg Ala Ala Arg Ala Gly Gly Pro Gly
                100                 105                 110
```

```
Ser Arg Ala Arg Ala Ala Gly Ala Arg Gly Cys Arg Leu Arg Ser Gln
        115                 120                 125

Leu Val Pro Val Arg Ala Leu Gly Leu Gly His Arg Ser Asp Glu Leu
130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
            180                 185                 190

Tyr Glu Ala Val Ser Phe Met Asp Val Asn Ser Thr Trp Arg Thr Val
        195                 200                 205

Asp Arg Leu Ser Ala Thr Ala Cys Gly Cys Leu Gly
210                 215                 220

<210> SEQ ID NO 11
<211> LENGTH: 224
<212> TYPE: PRT
<213> ORGANISM: Mus musculus

<400> SEQUENCE: 11

Met Glu Leu Gly Leu Ala Glu Pro Thr Ala Leu Ser His Cys Leu Arg
1               5                   10                  15

Pro Arg Trp Gln Ser Ala Trp Trp Pro Thr Leu Ala Val Leu Ala Leu
            20                  25                  30

Leu Ser Cys Val Thr Glu Ala Ser Leu Asp Pro Met Ser Arg Ser Pro
        35                  40                  45

Ala Ala Arg Asp Gly Pro Ser Pro Val Leu Ala Pro Pro Thr Asp His
    50                  55                  60

Leu Pro Gly Gly His Thr Ala His Leu Cys Ser Glu Arg Thr Leu Arg
65                  70                  75                  80

Pro Pro Pro Gln Ser Pro Gln Pro Ala Pro Pro Pro Gly Pro Ala
                85                  90                  95

Leu Gln Ser Pro Pro Ala Ala Leu Arg Gly Ala Arg Ala Ala Arg Ala
            100                 105                 110

Gly Thr Arg Ser Ser Arg Ala Arg Thr Thr Asp Ala Arg Gly Cys Arg
        115                 120                 125

Leu Arg Ser Gln Leu Val Pro Val Ser Ala Leu Gly Leu Gly His Ser
130                 135                 140

Ser Asp Glu Leu Ile Arg Phe Arg Phe Cys Ser Gly Ser Cys Arg Arg
145                 150                 155                 160

Ala Arg Ser Gln His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
            180                 185                 190

Arg Pro Thr Arg Tyr Glu Ala Val Ser Phe Met Asp Val Asn Ser Thr
        195                 200                 205

Trp Arg Thr Val Asp His Leu Ser Ala Thr Ala Cys Gly Cys Leu Gly
210                 215                 220

<210> SEQ ID NO 12
<211> LENGTH: 224
<212> TYPE: PRT
<213> ORGANISM: Rattus norvegicus

<400> SEQUENCE: 12
```

```
Met Glu Leu Gly Leu Gly Glu Pro Thr Ala Leu Ser His Cys Leu Arg
 1               5                  10                  15
Pro Arg Trp Gln Pro Ala Leu Trp Pro Thr Leu Ala Ala Leu Ala Leu
             20                  25                  30
Leu Ser Ser Val Thr Glu Ala Ser Leu Asp Pro Met Ser Arg Ser Pro
         35                  40                  45
Ala Ser Arg Asp Val Pro Ser Pro Val Leu Ala Pro Pro Thr Asp Tyr
 50                  55                  60
Leu Pro Gly Gly His Thr Ala His Leu Cys Ser Glu Arg Ala Leu Arg
 65                  70                  75                  80
Pro Pro Pro Gln Ser Pro Gln Pro Ala Pro Pro Gly Pro Ala
                 85                  90                  95
Leu Gln Ser Pro Pro Ala Ala Leu Arg Gly Ala Arg Ala Ala Arg Ala
                100                 105                 110
Gly Thr Arg Ser Ser Arg Ala Arg Ala Thr Asp Ala Arg Gly Cys Arg
             115                 120                 125
Leu Arg Ser Gln Leu Val Pro Val Ser Ala Leu Gly Leu Gly His Ser
130                 135                 140
Ser Asp Glu Leu Ile Arg Phe Arg Phe Cys Ser Gly Ser Cys Arg Arg
145                 150                 155                 160
Ala Arg Ser Pro His Asp Leu Ser Leu Ala Ser Leu Leu Gly Ala Gly
                 165                 170                 175
Ala Leu Arg Ser Pro Pro Gly Ser Arg Pro Ile Ser Gln Pro Cys Cys
             180                 185                 190
Arg Pro Thr Arg Tyr Glu Ala Val Ser Phe Met Asp Val Asn Ser Thr
             195                 200                 205
Trp Arg Thr Val Asp His Leu Ser Ala Thr Ala Cys Gly Cys Leu Gly
210                 215                 220
```

<210> SEQ ID NO 13
<211> LENGTH: 130
<212> TYPE: PRT
<213> ORGANISM: Artificial Sequence
<220> FEATURE:
<223> OTHER INFORMATION: Synthetically generated peptide

<400> SEQUENCE: 13

```
Met Ala Thr Gly Ser Arg Thr Ser Leu Leu Leu Ala Phe Gly Leu Leu
 1               5                  10                  15
Cys Leu Ser Trp Leu Gln Glu Gly Ser Ala Ala Gly Ala Arg Gly
             20                  25                  30
Cys Arg Leu Arg Ser Gln Leu Val Pro Val Arg Ala Leu Gly Leu Gly
         35                  40                  45
His Arg Ser Asp Glu Leu Val Arg Phe Arg Phe Cys Ser Gly Ser Cys
     50                  55                  60
Arg Arg Ala Arg Ser Pro His Asp Leu Ser Leu Ala Ser Leu Leu Gly
 65                  70                  75                  80
Ala Gly Ala Leu Arg Pro Pro Gly Ser Arg Pro Val Ser Gln Pro
                 85                  90                  95
Cys Cys Arg Pro Thr Arg Tyr Glu Ala Val Ser Phe Met Asp Val Asn
                100                 105                 110
Ser Thr Trp Arg Thr Val Asp Arg Leu Ser Ala Thr Ala Cys Gly Cys
             115                 120                 125
Leu Gly
130
```

-continued

```
<210> SEQ ID NO 14
<211> LENGTH: 130
<212> TYPE: PRT
<213> ORGANISM: Artificial Sequence
<220> FEATURE:
<223> OTHER INFORMATION: Synthetically generated peptide

<400> SEQUENCE: 14

Met Ala Thr Gly Ser Arg Thr Ser Leu Leu Leu Ala Phe Gly Leu Leu
 1               5                  10                  15

Cys Leu Ser Trp Leu Gln Glu Gly Ser Ala Ala Ala Gly Ala Arg Gly
            20                  25                  30

Cys Arg Leu Arg Ser Gln Leu Val Pro Val Arg Ala Leu Gly Leu Gly
        35                  40                  45

His Arg Ser Asp Glu Leu Val Arg Phe Arg Phe Cys Ser Gly Ser Cys
    50                  55                  60

Glu Glu Ala Arg Ser Pro His Asp Leu Ser Leu Ala Ser Leu Leu Gly
65                  70                  75                  80

Ala Gly Ala Leu Arg Pro Pro Pro Gly Ser Arg Pro Val Ser Gln Pro
                85                  90                  95

Cys Cys Arg Pro Thr Arg Tyr Glu Ala Val Ser Phe Met Asp Val Asn
            100                 105                 110

Ser Thr Trp Arg Thr Val Asp Arg Leu Ser Ala Thr Ala Cys Gly Cys
        115                 120                 125

Leu Gly
    130
```

NEUBLASTIN VARIANTS

CROSS REFERENCE TO RELATED APPLICATIONS

This application is a national phase filing under 35 U.S.C. §371 of international application number PCT/US2005/029637, filed Aug. 18, 2005, which claims priority from provisional application No. 60/602,825, filed Aug. 19, 2004 and provisional application No. 60/694,067, filed Jun. 24, 2005. The entire content of each of these prior applications is incorporated herein by reference in its entirety.

TECHNICAL FIELD

The invention relates to protein chemistry, molecular biology, and neurobiology.

BACKGROUND

Neublastin, also known as Artemin and Enovin, is a 24-kDa homodimeric secreted protein that promotes the survival of neurons of the peripheral and central nervous system such as dopaminergic neurons (Baudet et al., 2000, *Development*, 127:4335; Rosenblad et al., 2000, *Mol. Cell Neurosci.*, 15(2):199; GenBank AF120274). The gene encoding neublastin has been cloned and sequenced (Roseblad et al., 2000, *Mol. Cell Neurosci.*, 15(2):199; Baloh et al., *Neuron*, 21:1291).

Neublastin is a member of the glial cell line-derived neurotrophic factor (GDNF) ligand family. At the cellular level, GDNF members activate the receptor tyrosine kinase, RET. RET associates with a co-receptor, GDNF family receptor alpha (GFRalpha), a glycosylphosphatidyl inositol (GPI) linked membrane protein that provides ligand specificity for RET. Four GFRalphas are known (GFRalpha1-4). Neublastin binds to GFRalpha3 together with RET forming a ternary signaling complex (Baudet et al. 2000, *Development*, 127: 4335; Baloh et al., 1998, *Neuron*, 21:1291), which is localized predominantly on nociceptive sensory neurons (Orozco et al., 2001, *Eur. J. Neurosci.*, 13(11):2177). These neurons detect pain and injury. Thus, neublastin has clinical application in the general treatment of neuropathy and more specifically in the treatment of neuropathic pain.

Neublastin and the other GDNF family members are members of the transforming growth factor beta (TGF beta) superfamily and thus, are characterized by the presence of seven conserved cysteine residues with similar spacing which form the structure of a cysteine knot (Saarma, 1999, *Microsc. Res. Tech.*, 45:292). Each monomer contains two disulfide bonds that form a closed loop structure encircling the third disulfide to form a tight knot structure. The seventh cysteine contained within each monomer forms an intermolecular disulfide bond, covalently linking the monomers to form the final dimer product (Rattenholl et al 2000, *J. Mol. Biol.*, 305:523).

TGF beta family members are synthesized as pre pro proteins that eventually are secreted as a mature homodimer after cleavage of the signal peptide and pro-domain (see e.g. Rattenholl, et al., 2000, *J. Mol. Biol.*, 305:523; Fairlie et al., 2001, *J. Biol. Chem.*, 276(20): 16911). Both the signal peptide and pro-domain mediate proper secretion for TGF beta family members (Rattenholl et al., 2000, *J. Mol. Biol.*, 305:523; Rattenholl et al., 2001, *Eur. J. Biochem.*, 268:3296).

SUMMARY

The invention is based, at least in part, on the discovery that Neublastin binds to heparin sulfate and that particular amino acid residues in the Neublastin polypeptide contribute to this binding event. Substitution of selected amino acid residues was found to decrease heparin binding by variant Neublastin polypeptides and increase bioactivity and bioavailability of the variants.

In one aspect, the invention features a polypeptide containing an amino acid sequence that is at least 80% identical to amino acids 15-113 of SEQ ID NO:1, wherein the amino acid sequence contains at least one amino acid substitution, relative to SEQ ID NO:1, selected from the group consisting of: (i) an amino acid other than arginine at the position corresponding to position 48 of SEQ ID NO:1 (e.g., the arginine is substituted with a non-conservative amino acid residue such as glutamic acid); (ii) an amino acid other than arginine at the position corresponding to position 49 of SEQ ID NO:1 (e.g., the arginine is substituted with a non-conservative amino acid residue such as glutamic acid); and (iii) an amino acid other than arginine at the position corresponding to position 51 of SEQ ID NO:1 (e.g., the arginine is substituted with a non-conservative amino acid residue such as glutamic acid). The polypeptide, when dimerized, binds to a complex containing GFRalpha3 and RET.

In some embodiments, the amino acid sequence contains amino acids other than arginine at the positions corresponding to position 48 and position 49 of SEQ ID NO:1. For example, the arginine residue at position 48 and the arginine reside at position 49 of SEQ ID NO:1 can be substituted with non-conservative amino acid residues (e.g., glutamic acid).

In some embodiments, the amino acid sequence is at least 90%, at least 95%, or at least 98% identical to amino acids 15-113 of SEQ ID NO:1.

Also disclosed is a polypeptide containing amino acids 15-113 of SEQ ID NO:2, amino acids 15-113 of SEQ ID NO:3, amino acids 15-113 of SEQ ID NO:4, amino acids 15-113 of SEQ ID NO:5, amino acids 15-113 of SEQ ID NO:8, or amino acids 15-113 of SEQ ID NO:9. In some embodiments, the polypeptide contains amino acids 10-113 of SEQ ID NO:2, amino acids 10-113 of SEQ ID NO:3, amino acids 10-113 of SEQ ID NO:4, amino acids 10-113 of SEQ ID NO:5, amino acids 10-113 of SEQ ID NO:8, or amino acids 10-113 of SEQ ID NO:9. In some embodiments, the polypeptide contains the amino acid sequence of SEQ ID NO:2, the amino acid sequence of SEQ ID NO:3, the amino acid sequence of SEQ ID NO:4, the amino acid sequence of SEQ ID NO:5, the amino acid sequence of SEQ ID NO:8, or the amino acid sequence of SEQ ID NO:9.

Also disclosed is a polypeptide containing an amino acid sequence at least 80% identical to amino acids 15-113 of SEQ ID NO:1, wherein the amino acid sequence comprises at least one amino acid substitution, relative to SEQ ID NO:1, selected from the group consisting of: (i) an amino acid other than serine at the position corresponding to position 20 of SEQ ID NO:1 (e.g., the serine is substituted with a non-conservative amino acid residue); (ii) an amino acid other than glutamine at the position corresponding to position 21 of SEQ ID NO:1 (e.g., the glutamine is substituted with a non-conservative amino acid residue); (iii) an amino acid other than histidine at the position corresponding to position 32 of SEQ ID NO:1 (e.g., the histidine is substituted with a non-conservative amino acid residue); (iv) an amino acid other than arginine at the position corresponding to position 33 of SEQ ID NO:1 (e.g., the arginine is substituted with a non-conservative amino acid residue); (v) an amino acid other than arginine at the position corresponding to position 39 of SEQ ID NO:1 (e.g., the arginine is substituted with a non-conservative amino acid residue); (vi) an amino acid other than serine at the position corresponding to position 46 of SEQ ID NO:1 (e.g., the serine is substituted with a non-conservative amino acid residue); (vii) an amino acid other than arginine at the position corresponding to position 68 of SEQ ID NO:1 (e.g., the arginine is substituted with a non-conservative amino acid residue); (viii) an amino acid other than glycine at the position corresponding to position 72 of SEQ ID NO:1 (e.g., the glycine is substituted with a non-conservative amino acid residue); (ix) an amino acid other than serine at the position corresponding to position 73 of SEQ ID NO:1 (e.g., the serine is substituted with a non-conservative amino acid residue); and (x) an amino acid other than valine at the position corresponding to position 94 of SEQ ID NO:1 (e.g., the valine is substituted with a non-conservative amino acid residue). The polypeptide, when dimerized, binds to a complex containing GFRalpha3 and RET. In some embodiments, the amino acid sequence is at least 90%, at least 95%, or at least 98% identical to amino acids 15-113 of SEQ ID NO:1.

Also disclosed is a polypeptide containing an amino acid sequence at least 80% identical to SEQ ID NO:1, wherein the amino acid sequence comprises at least one amino acid substitution, relative to SEQ ID NO:1, selected from the group consisting of: (i) an amino acid other than arginine at the position corresponding to position 7 of SEQ ID NO:1 (e.g., the arginine is substituted with a non-conservative amino acid residue such as glutamic acid); (ii) an amino acid other than arginine at the position corresponding to position 9 of SEQ ID NO:1 (e.g., the arginine is substituted with a non-conservative amino acid residue such as glutamic acid); and (iii) an amino acid other than arginine at the position corresponding to position 14 of SEQ ID NO:1 (e.g., the arginine is substituted with a non-conservative amino acid residue such as glutamic acid). The polypeptide, when dimerized, binds to a complex containing GFRalpha3 and RET. In some embodiments, the amino acid sequence is at least 90%, at least 95%, or at least 98% identical to SEQ ID NO:1.

The invention also features conjugates containing a polypeptide described herein conjugated to a non-naturally occurring polymer. An exemplary polymer is a water-soluble synthetic polymer such as a polyalkylene glycol (e.g., polyethylene glycol).

The invention also features a fusion protein containing a polypeptide described herein and a heterologous amino acid sequence.

The invention also features a dimer containing two of the polypeptides, conjugates, or fusion proteins described herein.

The invention also features a pharmaceutical composition containing a polypeptide, dimer, conjugate, or fusion protein described herein and a pharmaceutically acceptable carrier or excipient.

Also disclosed is a nucleic acid containing a sequence that encodes a polypeptide described herein, an expression vector containing the nucleic acid, and a cell containing the expression vector.

Also disclosed is a method of making a polypeptide, the method including the following steps: (i) providing a cell containing an expression vector containing a nucleic acid encoding a polypeptide described herein, and (ii) culturing the cell under conditions that permit expression of the nucleic acid.

The invention also features a method of treating or preventing a nervous system disorder in a mammal by administering to the mammal a therapeutically effective amount of a polypeptide, dimer, conjugate, fusion protein, or pharmaceutical composition described herein.

The invention also features a method of treating neuropathic pain in a mammal by administering to the mammal a therapeutically effective amount of a polypeptide, dimer, conjugate, fusion protein, or pharmaceutical composition described herein.

The invention also features a method of activating the RET receptor in a mammal by administering to the mammal an effective amount of a polypeptide, dimer, conjugate, fusion protein, or pharmaceutical composition described herein.

An advantage of selected variant Neublastin polypeptides described herein is that they have decreased heparin binding ability as compared to wild type Neublastin. Decreased heparin binding results in a decreased clearance of the variant polypeptide in vivo.

A variant Neublastin polypeptide having substitutions at amino acid positions 48 and 49 was unexpectedly found to have greatly deceased heparin binding ability and greatly increased potency and bioavailability as compared to single amino acid mutants and/or wild type Neublastin. For example, the double mutant was found to exhibit an approximately 185-fold increase in serum exposure as compared to wild type Neublastin. In addition, this double mutant was found to exhibit an over five fold increase in expression in vitro as compared to wild type Neublastin, thereby facilitating large scale production of the protein.

The advantages and unexpected properties of the variant Neublastin polypeptides allow for treatment of subjects using lower doses of protein and/or allow for lengthened intervals between administrations (as compared to treatments with the wild type protein).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is an alignment of wild type human (SEQ ID NO:10), mouse (SEQ ID NO:11), and rat (SEQ ID NO:12) pre pro Neublastin polypeptides. The left and right vertical lines indicate, respectively, the start of the mature 113 amino and 104 amino acid forms. The RRXR heparin binding motif is boxed.

FIG. 9 is a graph depicting the results of ternary complex analysis of wild type Neublastin, Arg48E, Arg49E, Arg51E, Arg48,49E, and Arg48,49,51E Neublastin forms.

DETAILED DESCRIPTION

Figure 2A:
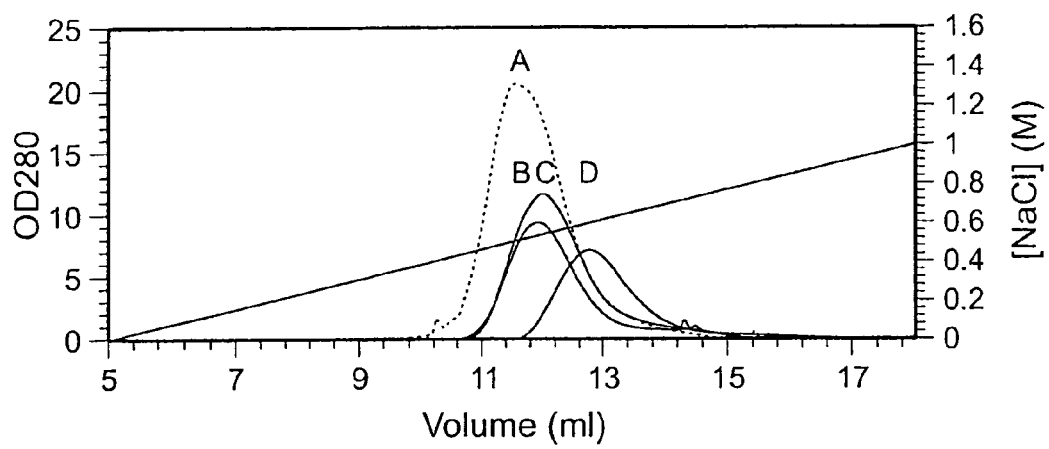
FIG. 2A depicts a cationic elution profile of wild-type Neublastin (Peak D) and three single Arg-to-Glu substitution mutants (Peaks A, B, and C) (sloping line represents the theoretical sodium chloride concentration for any given volume eluted from the column). Data are a representation of the OD280 values of the eluted sample.

The present invention provides variant Neublastin polypeptides having substitutions at selected amino acid residues. As disclosed in the accompanying Examples, specific residues in the wild type Neublastin polypeptide have been found to be important for heparin binding. Because heparin binding is believed to contribute to clearance of Neublastin in vivo, substitutions at one or more of these specific residues are expected to decrease heparin binding and thereby increase serum exposure of the variant polypeptide.

Variant Neublastin Polypeptides

Mature wild type human Neublastin is 113 amino acids in length and has the following amino acid sequence: AGGPG-SRARAAGARGCRLRSQLVPVRALGLGH-RSDELVRFRFCSGSCRRARSPH-DLSLASLLGAGALRPPPGSRPVSQPCCRPTRYEAVS-FMDVNSTWRTVDRLSATACGCLG (SEQ ID NO:1).

Disclosed herein are polypeptides that have substitutions at one or more selected amino acid residues of the Neublastin polypeptide. Mutations at one or more of these residues are expected to result in a variant Neublastin polypeptide having reduced or absent heparin binding ability as compared to wild type Neublastin. A variant Neublastin polypeptide contains an amino acid substitution, relative to SEQ ID NO:1, at (i) an arginine residue at one or more of positions 48, 49, or 51, and/or (ii) one or more of Ser 46, Ser 73, Gly 72, Arg 39, Gln 21, Ser 20, Arg 68, Arg 33, His 32, Val 94, Arg 7, Arg 9, or Arg 14. Unless otherwise stated, any reference herein to a Neublastin amino acid reside by position number refers to the numbering of residues relative to SEQ ID NO:1.

A Neublastin amino acid residue designated for substitution (e.g., an arginine residue at position 48, 49, and/or 51) can be substituted with a non-conservative amino acid residue (e.g., glutamic acid) or a conservative or amino acid residue. As detailed in the accompanying Examples, substitution of Arg48, Arg 49, and/or Arg 51 with a non-conservative amino acid can result in a variant Neublastin polypeptide that has reduced heparin binding activity but retained (or even enhanced) Neublastin biological activity. Exemplary amino acids that can be substituted an amino acid residue identified herein (e.g., an arginine residue at position 48, 49, and/or 51) include glutamic acid, aspartic acid, and alanine.

A biologically active variant Neublastin polypeptide, when dimerized, binds to a ternary complex containing GFRalpha3 and RET. Any method for detecting binding to this complex can be used to evaluate the biological activity a variant Neublastin polypeptide. Exemplary assays for detecting the ternary complex-binding ability of a variant Neublastin polypeptide are described in WO00/001815 and in Example 7.

A variant Neublastin polypeptide can also be assessed to evaluate its ability to trigger the Neublastin signaling cascade. For example, the Kinase Receptor Activation (KIRA) assay described in Example 6 can be used to assess the ability of a variant Neublastin polypeptide to induce RET autophosphorylation (See also, Sadick et al., 1996, *Anal. Biochem.*, 235 (2):207).

In addition to the specific amino acid substitutions identified herein, a variant Neublastin polypeptide can also contain one or more additions, substitutions, and/or deletions at other amino acid positions, as detailed in the following sections.

A variant Neublastin polypeptide can, in addition to having one or more of the amino acid substitutions described herein, also vary in length. Although the mature human Neublastin polypeptide (SEQ ID NO:1) consists of the carboxy terminal 113 amino acids of pre pro Neublastin, not all of the 113 amino acids are required to achieve useful Neublastin biological activity. Amino terminal truncation is permissible. Thus, a variant Neublastin polypeptide can contain one or more of the amino acid substitutions described herein in the context of the carboxy terminal 99, 100, 101, 102, 103, 104, 105, 106, 107, 108, 109, 110, 111, 112, or 113 amino acids of SEQ ID NO:1 (i.e., its length can be 99, 100, 101, 102, 103, 104, 105, 106, 107, 108, 109, 110, 111, 112, or 113 amino acids).

A variant Neublastin polypeptide can, in addition to having one or more of the amino acid substitutions described herein (and optionally having a truncation described herein), also vary in sequence. In particular, certain amino acid substitutions can be introduced into the Neublastin sequence without appreciable loss of a Neublastin biological activity. In exemplary embodiments, a polypeptide (i) contains one or more of the amino acid substitutions described herein, and (ii) is at least 70%, 80%, 85%, 90%, 95%, 98% or 99% identical to SEQ ID NO:1 (or 70%, 80%, 85%, 90%, 95%, 98% or 99% identical to amino acids 15-113 of SEQ ID NO:1). A variant Neublastin polypeptide differing in sequence from SEQ ID NO:1 (or differing in sequence from amino acids 15-113 of SEQ ID NO:1) may include one or more conservative amino acid substitutions, one or more non-conservative amino acid substitutions, and/or one or more deletions or insertions.

FIG. 1 is an alignment of the wild type human, mouse, and rat pre pro Neublastin polypeptides. The vertical lines in FIG. 1 indicate the start of the mature 113 amino acid form (left vertical line) and 104 amino acid form (right vertical line) of Neublastin. The RRXR heparin binding motif is boxed. This alignment of naturally occurring, bioactive forms of Neublastin indicates specific exemplary residues (i.e., those that are not conserved among the human, mouse, and rat forms) that can be substituted without eliminating bioactivity.

Percent identity between amino acid sequences can be determined using the BLAST 2.0 program. Sequence comparison can be performed using an ungapped alignment and using the default parameters (Blossom 62 matrix, gap existence cost of 11, per residue gap cost of 1, and a lambda ratio of 0.85). The mathematical algorithm used in BLAST programs is described in Altschul et al., 1997, *Nucleic Acids Research* 25:3389-3402.

A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, Ile, Phe or Trp) is substituted for, or by, one having a smaller side chain (e.g., Ala, Ser) or no side chain (e.g., Gly).

Exemplary variant Neublastin polypeptides are disclosed in Table 1. Amino acid residues of the variant Neublastin polypeptides that are mutated as compared to the corresponding wild type position are bolded and underlined. In addition, the Neublastin polypeptide (113, 99, or 104 amino acids in length) used as the background for the substitution is depicted in Table 1.

TABLE 1

Variant Neublastin Polypeptides

| SEQ ID NO | Position Substituted | Length of Polypeptide | Amino Acid Sequence |
|---|---|---|---|
| 2 | Arg 48 | 113 | AGGPGSRARAAGARGCRLRSQLVPVRALGLGHRSDELVRFRFCSGSCERARSPHDLSLASLLGAGALRPPPGSRPVSQPCCRPTRYEAVSFMDVNSTWRTVDRLSATACGCLG |
| 3 | Arg 49 | 113 | AGGPGSRARAAGARGCRLRSQLVPVRALGLGHRSDELVRFRFCSGSCREARSPHDLSLASLLGAGALRPPPGSRPVSQPCCRPTRYEAVSFMDVNSTWRTVDRLSATACGCLG |
| 4 | Arg 51 | 113 | AGGPGSRARAAGARGCRLRSQLVPVRALGLGHRSDELVRFRFCSGSCRRAESPHDLSLASLLGAGALRPPPGSRPVSQPCCRPTRYEAVSFMDVNSTWRTVDRLSATACGCLG |
| 5 | Arg 48 and Arg 49 | 113 | AGGPGSRARAAGARGCRLRSQLVPVRALGLGHRSDELVRFRFCSGSCEEARSPHDLSLASLLGAGALRPPPGSRPVSQPCCRPTRYEAVSFMDVNSTWRTVDRLSATACGCLG |
| 6 | Arg 48 and Arg 49 | 99 | GCRLRSQLVPVRALGLGHRSDELVRFRFCSGSCEEARSPHDLSLASLLGAGALRPPPGSRPVSQPCCRPTRYEAVSFMDVNSTWRTVDRLSATACGCLG |
| 7 | Arg 48 and Arg 49 | 104 | AAGARGCRLRSQLVPVRALGLGHRSDELVRFRFCSGSCEEARSPHDLSLASLLGAGALRPPPGSRPVSQPCCRPTRYEAVSFMDVNSTWRTVDRLSATACGCLG |
| 8 | Arg 49 and Arg 51 | 113 | AGGPGSRARAAGARGCRLRSQLVPVRALGLGHRSDELVRFRFCSGSCREAESPHDLSLASLLGAGALRPPPGSRPVSQPCCRPTRYEAVSFMDVNSTWRTVDRLSATACGCLG |

TABLE 1-continued

Variant Neublastin Polypeptides

| SEQ ID NO | Position Substituted | Length of Polypeptide | Amino Acid Sequence |
|---|---|---|---|
| 9 | Arg 48 and Arg 51 | 113 | AGGPGSRARAAGARGCRLRSQLVPVRA LGLGHRSDELVRFRFCSGSCERAESPHD LSLASLLGAGALRPPPGSRPVSQPCCRPT RYEAVSFMDVNSTWRTVDRLSATACGC LG |

A variant Neublastin polypeptide can be optionally coupled to a polymer (e.g., a polyalkylene glycol moiety such as a polyethylene glycol moiety). In some embodiments, the polymer is coupled to the polypeptide at a site on the Neublastin polypeptide that is an N terminus. In some embodiments, the variant Neublastin polypeptide includes at least one amino acid substitution with respect to SEQ ID NO:1 (or with respect to amino acids 15-113 of SEQ ID NO:1), which provides an internal polymer conjugation site to which a polymer can be conjugated. In some embodiments, the polymer is coupled to the variant Neublastin polypeptide at a residue (numbered in accordance with the sequence of SEQ ID NO:1) selected from the group consisting of position 14, position 39, position 68, and position 95. Exemplary Neublastin variants that provide internal polymer conjugation sites are described in WO 02/060929 and WO 04/069176 (the contents of which are incorporated herein by reference).

A polypeptide can optionally contain heterologous amino acid sequences in addition to a variant Neublastin polypeptide. "Heterologous," as used when referring to an amino acid sequence, refers to a sequence that originates from a source foreign to the particular host cell, or, if from the same host cell, is modified from its original form. Exemplary heterologous sequences include a heterologous signal sequence (e.g., native rat albumin signal sequence, a modified rat signal sequence, or a human growth hormone signal sequence) or a sequence used for purification of a variant Neublastin polypeptide (e.g., a histidine tag).

Neublastin polypeptides can be isolated using methods known in the art. Naturally occurring Neublastin polypeptides can be isolated from cells or tissue sources using standard protein purification techniques. Alternatively, mutated Neublastin polypeptides can be synthesized chemically using standard peptide synthesis techniques. The synthesis of short amino acid sequences is well established in the peptide art. See, e.g., Stewart, et al., Solid Phase Peptide Synthesis (2d ed., 1984).

In some embodiments, variant Neublastin polypeptides are produced by recombinant DNA techniques. For example, a nucleic acid molecule encoding a variant Neublastin polypeptide can be inserted into a vector, e.g., an expression vector, and the nucleic acid can be introduced into a cell. Suitable cells include, e.g., mammalian cells (such as human cells or CHO cells), fungal cells, yeast cells, insect cells, and bacterial cells. When expressed in a recombinant cell, the cell is preferably cultured under conditions allowing for expression of a variant Neublastin polypeptide. The variant Neublastin polypeptide can be recovered from a cell suspension if desired. As used herein, "recovered" means that the mutated polypeptide is removed from those components of a cell or culture medium in which it is present prior to the recovery process. The recovery process may include one or more refolding or purification steps.

Variant Neublastin polypeptides can be constructed using any of several methods known in the art. One such method is site-directed mutagenesis, in which a specific nucleotide (or, if desired a small number of specific nucleotides) is changed in order to change a single amino acid (or, if desired, a small number of predetermined amino acid residues) in the encoded variant Neublastin polypeptide. Many site-directed mutagenesis kits are commercially available. One such kit is the "Transformer Site Directed Mutagenesis Kit" sold by Clontech Laboratories (Palo Alto, Calif.).

Pharmaceutical Compositions

A variant Neublastin polypeptide can be incorporated into a pharmaceutical composition containing a therapeutically effective amount of the polypeptide and one or more adjuvants, excipients, carriers, and/or diluents. Acceptable diluents, carriers and excipients typically do not adversely affect a recipient's homeostasis (e.g., electrolyte balance). Acceptable carriers include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., REMINGTON'S PHARMACEUTICAL SCIENCES (Maack Publishing Co., Easton, Pa.).

Administration of a pharmaceutical composition containing a variant Neublastin polypeptide can be systemic or local. Pharmaceutical compositions can be formulated such that they are suitable for parenteral and/or non-parenteral administration. Specific administration modalities include subcutaneous, intravenous, intramuscular, intraperitoneal transdermal, intrathecal, oral, rectal, buccal, topical, nasal, ophthalmic, intra-articular, intra-arterial, sub-arachnoid, bronchial, lymphatic, vaginal, and intra-uterine administration.

Formulations suitable for parenteral administration conveniently contain a sterile aqueous preparation of the variant Neublastin polypeptide, which preferably is isotonic with the blood of the recipient (e.g., physiological saline solution). Formulations may be presented in unit-dose or multi-dose form.

An exemplary formulation contains a variant Neublastin polypeptide described herein and the following buffer components: sodium succinate (e.g., 10 mM); NaCl (e.g., 75 mM); and L-arginine (e.g., 100 mM).

Formulations suitable for oral administration may be presented as discrete units such as capsules, cachets, tablets, or lozenges, each containing a predetermined amount of the variant Neublastin polypeptide; or a suspension in an aqueous liquor or a non-aqueous liquid, such as a syrup, an elixir, an emulsion, or a draught.

Therapeutically effective amounts of a pharmaceutical composition may be administered to a subject in need thereof in a dosage regimen ascertainable by one of skill in the art. For example, a composition can be administered to the subject, e.g., systemically at a dosage from 0.01 µg/kg to 1000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, a variant Neublastin polypeptide is first administered at different dosing regimens. The unit dose and regimen depend on factors that include, e.g., the species of mammal, its immune status, the body weight of the mammal. Typically, protein levels in tissue are monitored using appropriate screening assays as part of a clinical testing procedure, e.g., to determine the efficacy of a given treatment regimen.

The frequency of dosing for a variant Neublastin polypeptide is within the skills and clinical judgement of physicians. Typically, the administration regime is established by clinical trials which may establish optimal administration parameters. However, the practitioner may vary such administration regimes according to the subject's age, health, weight, sex and medical status. The frequency of dosing may also vary between acute and chronic treatments for neuropathy. In addition, the frequency of dosing may be varied depending on whether the treatment is prophylactic or therapeutic.

Methods of Treatment

Variant Neublastin polypeptides are useful for modulating metabolism, growth, differentiation, or survival of a nerve or neuronal cell. In particular, variant Neublastin polypeptides can be used to treat or alleviate a disorder or disease of a living animal, e.g., a human, which disorder or disease is responsive to the activity of a neurotrophic agent.

The variant Neublastin polypeptides disclosed herein (and pharmaceutical compositions comprising same) can be used in methods for treating a disorder characterized by damage to sensory neurons or retinal ganglion cells, including neurons in the dorsal root ganglia or in any of the following tissues: the geniculate, petrosal and nodose ganglia; the vestibuloacoustic complex of the eighth cranial nerve; the ventrolateral pole of the maxillomandibular lobe of the trigeminal ganglion; and the mesencephalic trigeminal nucleus.

In some embodiments, sensory and/or autonomic system neurons can be treated. In particular, nociceptive and mechanoreceptive neurons can be treated, more particularly A-delta fiber, C-fiber and A-beta fiber neurons. In addition, sympathetic and parasympathetic neurons of the autonomic system can be treated.

In some embodiments, motor neuron diseases such as amyotrophic lateral sclerosis ("ALS") and spinal muscular atrophy can be treated. In other embodiments, the variant Neublastin polypeptides can be used to enhance nerve recovery following traumatic injury. Alternatively, or in addition, a nerve guidance channel with a matrix containing polymer-conjugated Neublastin polypeptides, or fusion or conjugates of mutated Neublastin polypeptides can be used. Such nerve guidance channels are disclosed, e.g., U.S. Pat. No. 5,834,029.

In some embodiments, the variant Neublastin polypeptides (and pharmaceutical compositions comprising same) are used in the treatment of various disorders in the eye, including photoreceptor loss in the retina in patients afflicted with macular degeneration, retinitis pigmentosa, glaucoma, and similar diseases.

In some embodiments, the variant Neublastin polypeptides (and pharmaceutical compositions comprising same) are used for treating neuropathic pain, for treating tactile allodynia, for reducing loss of pain sensitivity associated with neuropathy, for treating viral infections and viral-associated neuropathies, for treating painful diabetic neuropathy, and for treating nervous system disorders. The methods are discussed in detail in the following subsections.

1. Treatment of Neuropathic Pain

The variant Neublastin polypeptides disclosed herein (and pharmaceutical compositions comprising same) can be used in methods for treating neuropathic pain in a subject comprising administering to the subject an effective amount of a variant Neublastin polypeptide either alone, or by also administering to the subject an effective amount of an analgesia-inducing compound selected from the group consisting of opioids, anti-arrhythmics, topical analgesics, local anaesthetics, anticonvulsants, antidepressants, corticosteroids and non-steroidal anti-inflammatory drugs (NSAIDS). In one embodiment, the analgesia-inducing compound is an anticonvulsant. In another embodiment, the analgesia-inducing compound is gabapentin ((1-aminomethyl)cyclohexane acetic acid) or pregabalin (S-(+)-4-amino-3-(2-methylpropyl) butanoic acid).

The variant Neublastin polypeptides disclosed herein (and pharmaceutical compositions comprising same) can be used in the treatment of pain associated with peripheral neuropathies. Among the peripheral neuropathies which can be treated are trauma-induced neuropathies, e.g., those caused by physical injury or disease state, physical damage to the brain, physical damage to the spinal cord, stroke associated with brain damage, and neurological disorders related to neurodegeneration.

The variant Neublastin polypeptides disclosed herein (and pharmaceutical compositions comprising same) can be used in the treatment of a number of peripheral neuropathies, including: (a) trauma-induced neuropathies, (b) chemotherapy-induced neuropathies, (c) toxin-induced neuropathies (including but not limited to neuropathies induced by alcoholism, vitamin B6 intoxication, hexacarbon intoxication, amiodarone, chloramphenicol, disulfiram, isoniazide, gold, lithium, metronidazole, misonidazole, nitrofurantoin), (d) drug-induced neuropathies, including therapeutic drug-induced neuropathic pain (such as caused by anti-cancer agents, particularly anti-cancer agents selected from the group consisting of taxol, taxotere, cisplatin, nocodazole, vincristine, vindesine and vinblastine; and such as caused by anti-viral agents, particularly anti-viral agents selected from the group consisting of ddI, DDC, d4T, foscarnet, dapsone, metronidazole, and isoniazid), (e) vitamin-deficiency-induced neuropathies (including but not limited to vitamin B12 deficiency, vitamin B6 deficiency, and vitamin E deficiency), (f) idiopathic neuropathies, (g) diabetic neuropathies, (h) pathogen-induced nerve damage, (i) inflammation-induced nerve damage, (j) neurodegeneration, (k) hereditary neuropathy (including but not limited to Friedreich ataxia, familial amyloid polyneuropathy, Tangier disease, Fabry disease), (l) metabolic disorders (including but not limited to renal insufficiency and hypothyroidism), (m) infectious and viral neuropathies (including but not limited to neuropathic pain associated with leprosy, Lyme disease, neuropathic pain associated with infection by a virus, particularly a virus selected from the group consisting of a herpes virus (e.g. herpes zoster which may lead to post-herpetic neuralgia), a human immunodeficiency virus (HIV), and a papilloma virus), (n) auto-immune neuropathies (including but not limited to Guillain-Barre syndrome, chronic inflammatory demyelinating polyneuropathy, monoclonal gammopathy of undetermined significance and polyneuropathy), (o) trigeminal neuralgia and entrapment syndromes (including but not limited to Carpel tunnel), and (p) other neuropathic pain syndromes including post-traumatic neuralgia, phantom limb pain, multiple sclerosis pain, complex regional pain syndromes (including but not limited to reflex sympathetic dystrophy, causalgia), neoplasia-associated pain, vasculitic/angiopathic neuropathy, and sciatica. Neuropathic pain may be manifested as allodynia, hyperalgesia, spontaneous pain or phantom pain.

2. Treatment of Tactile Allodynia

The variant Neublastin polypeptides disclosed herein (and pharmaceutical compositions comprising same) can be used in the treatment of tactile allodynia in a subject. The term "tactile allodynia" typically refers to the condition in a subject where pain is evoked by stimulation of the skin (e.g. touch) that is normally innocuous.

In some embodiments, tactile allodynia is treated by administering to the subject a pharmaceutically effective amount of a variant Neublastin polypeptide. In a related embodiment, tactile allodynia may be treated by administering to a subject an effective amount of a variant Neublastin polypeptide either alone, or by administering to the subject an effective amount of a variant Neublastin polypeptide with an effective amount of an analgesia-inducing compound selected from the group consisting of opioids, anti-arrhythmics, topical analgesics, local anaesthetics, anticonvulsants, antidepressants, corticosteroids and NSAIDS. In one embodiment, the analgesia-inducing compound is an anticonvulsant. In another preferred embodiment, the analgesia-inducing compound is gabapentin ((1-aminomethyl)cyclohexane acetic acid) or pregabalin (S-(+)-4-amino-3-(2-methylpropyl)butanoic acid).

In some embodiments, a variant Neublastin polypeptide is administered in association with a therapeutic agent, including but not limited to an anti-cancer agent or an anti-viral agent. Anti-cancer agents include, but are not limited to, taxol, taxotere, cisplatin, nocodazole, vincristine, vindesine and vinblastine. Anti-viral agents include, but are not limited to, ddI, DDC, d4T, foscarnet, dapsone, metronidazole, and isoniazid.

3. Treatment for Reduction of Loss of Pain Sensitivity

In another embodiment, variant Neublastin polypeptides disclosed herein (and pharmaceutical compositions comprising same) can be used in a method for reducing the loss of pain sensitivity in a subject afflicted with a neuropathy. In one embodiment, the neuropathy is diabetic neuropathy. In some embodiments, the loss of pain sensitivity is a loss in thermal pain sensitivity. This methods include both prophylactic and therapeutic treatment.

In prophylactic treatment, a variant Neublastin polypeptide is administered to a subject at risk of developing loss of pain sensitivity (such a subject would be expected to be a subject with an early stage neuropathy). The treatment with a variant Neublastin polypeptide under such circumstances would serve to treat at-risk patients preventively.

In therapeutic treatment, a variant Neublastin polypeptide is administered to a subject who has experienced loss of pain sensitivity as a result of affliction with a neuropathy (such a subject would be expected to be a subject with a late stage neuropathy). The treatment with a variant Neublastin polypeptide under such circumstances would serve to rescue appropriate pain sensitivity in the subject.

4. Treatment of Viral Infections and Viral-Associated Neuropathies

Prophylactic treatment of infectious and viral neuropathies is contemplated. Prophylactic treatment is indicated after determination of viral infection and before onset of neuropathic pain. During treatment, a variant Neublastin polypeptide is administered to prevent appearance of neuropathic pain including but not limited to neuropathic pain associated with leprosy, Lyme disease, neuropathic pain associated with infection by a virus, particularly a virus selected from the group consisting of a herpes virus (and more particularly by a herpes zoster virus, which may lead to post-herpetic neuralgia), a human immunodeficiency virus (HIV), and a papilloma virus). In an alternative embodiment, a variant Neublastin polypeptide is administered to reduce the severity of neuropathic pain, should it appear.

Symptoms of acute viral infection often include the appearance of a rash. Other symptoms include, for example, the development of persistent pain in the affected area of the body, which is a common complication of a herpes zoster infection (shingles). Post-herpetic neuralgia can last for a month or more, and may appear several months after any rash-like symptoms have disappeared.

5. Treatment of Painful Diabetic Neuropathy

Prophylactic treatment of painful diabetic neuropathy is contemplated. Prophylactic treatment of diabetic neuropathies would commence after determination of the initial diagnosis of diabetes or diabetes-associated symptoms and before onset of neuropathic pain. Prophylactic treatment of painful diabetic neuropathy may also commence upon determining that a subject is at risk for developing diabetes or diabetes-associated symptoms. During treatment, a variant Neublastin polypeptide is administered to prevent appearance of neuropathic pain. In an alternative embodiment, a variant Neublastin polypeptide is administered to reduce the severity of neuropathic pain that has already appeared.

6. Treatment of Nervous System Disorders

The variant Neublastin polypeptides disclosed herein (and pharmaceutical compositions comprising same) can be used in the treatment or prevention of a nervous system disorder in a subject (such as a human), by administering to a subject in need thereof a therapeutically effective amount of a variant Neublastin polypeptide, a composition containing a variant Neublastin polypeptide, or a complex that includes a stable, aqueous soluble conjugated variant Neublastin polypeptide coupled to a polyalkylene moiety such as, e.g., PEG.

The nervous system disorder can be a peripheral nervous system disorder, such as a peripheral neuropathy or a neuropathic pain syndrome. Humans are preferred subjects for treatment.

A variant Neublastin polypeptide is useful for treating a defect in a neuron, including without limitation lesioned neurons and traumatized neurons. Peripheral nerves that experience trauma include, but are not limited to, nerves of the medulla or of the spinal cord. Variant Neublastin polypeptides are useful in the treatment of neurodegenerative disease, e.g., cerebral ischemic neuronal damage; neuropathy, e.g., peripheral neuropathy, Alzheimer's disease, Huntington's disease, Parkinson's disease, amyotrophic lateral sclerosis (ALS). Such variant Neublastin polypeptides can be used in the treatment of impaired memory, e.g., memory impairment associated with dementia.

The following are examples of the practice of the invention. They are not to be construed as limiting the scope of the invention in any way.

EXAMPLES

Example 1

Design and Synthesis of Variant Neublastin Polypeptides

Human Neublastin was crystallized and its structure revealed a triad of sulfate ions interacting with the following four Neublastin residues in close proximity to each other: Arg14, Arg48, Arg49, and Arg51. Based upon the presence of this triad and their relative spacing to one another, it was postulated that this region of Neublastin could be a potential heparin sulfate-binding domain. Subsequently, a previously solved heparin sulfate structure was docked (in-silico) to Neublastin at the site of the sulfate triad. Heparin sulfate fit precisely in this position, suggesting that this region within Neublastin has potential for heparin sulfate binding.

The Neublastin crystallization data also revealed that the following amino acid residues provide supplementary interactions with either the triad of sulfate ions or with one or more of three other sulfate ions that interact with Neublastin: Ser 46, Ser 73, Gly 72, Arg 39, Gln 21, Ser 20, Arg 68, Arg 33, His 32, and Val 94. In addition to the sulfate binding sites revealed by the crystal structure, Neublastin contains a heparin sulfate binding site consensus sequence (GPGSRAR) at residues 3-9 at its N-terminus. This region was unstructured in the crystal structure but may become ordered upon binding glycosaminoglycans. The region is likely to be close in space to the three sulfate cluster observed in the crystal structure (Arg14 contributes to the heparin-binding site that is mainly centered in the hinge region of the protein).

To investigate the biological relevance of the potential heparin sulfate-binding domain, three individual single amino acid residue substitutions were made within the mature 113 amino acid human Neublastin (SEQ ID NO:1). The arginine residues at each of position 48 (variant named "Arg48E"; SEQ ID NO:2), position 49 (variant named "Arg49E"; SEQ ID NO:3), and position 51 (variant named "Arg51E"; SEQ ID NO:4) were replaced by glutamate (i.e., three different single amino acid variant constructs were prepared) with the intention of changing the residue charge from one that would attract sulfate to one that would repel, and to potentially stabilize surrounding arginine residues. Proteins were refolded and purified from E. coli inclusion bodies (see WO 04/069176). Each Neublastin variant was subjected to analysis to verify structural integrity and confirm the correct residue substitution. All three mutants were structurally comparable to the wild-type human Neublastin.

Example 2

Cationic and Heparin Sepharose Chromatography

The variant Neublastin polypeptides were subjected to further biochemical analysis to determine the effect each mutation had on heparin binding. Heparin Sepharose and cationic chromatography were both employed. Since wild-type human Neublastin is a basic protein with an apparent pI of 11.31, Neublastin binds efficiently to cationic-based resins. A single conversion of arginine to glutamate decreases the apparent pI to 10.88. However, this lower pI was not expected to dramatically alter cationic resin-binding nor was it expected to alter the elution profile of the mutants compared to that of the wild-type control.

Each of the mutants (along with the wild-type Neublastin control) was subjected to cationic chromatography. The samples were loaded onto resin in buffer containing 5 mM phosphate pH 6.5 and 150 mM sodium chloride followed by elution with a linear salt gradient starting at 150 mM and ending with 1M sodium chloride. Wild-type Neublastin eluted at ~800 mM sodium chloride (FIG. 2A; Peak D), whereas each of the three mutants eluted within a salt range of approximately 500 mM, thus reflecting their lower pI. Arg49E and Arg51E (FIG. 2A; Peaks B and C) eluted with slightly higher salt than was required to elute Arg48E (FIG. 2A; Peak A) (520 mM vs 490 mM, respectively). This difference suggested that Arg48 is more surface accessible and contributes more to cationic binding than that of the other two mutations.

Figure 2B:
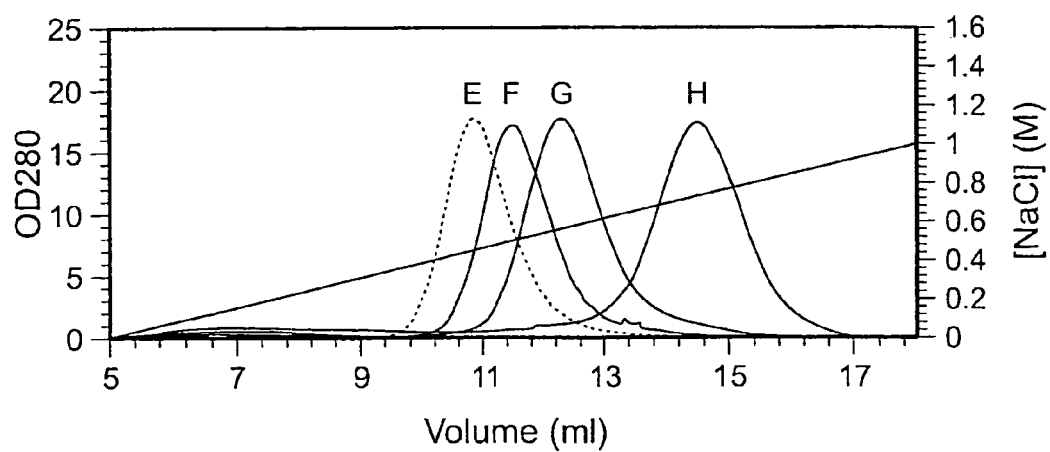
FIG. 2B depicts a Heparin Sepharose elution profile of wild-type Neublastin (Peak H) and three single Arg-to-Glu substitution mutants (Peaks E, F, and G) (sloping line represents the theoretical sodium chloride concentration for any given volume eluted from the column). Data are a representation of the OD280 values of the eluted sample.

To determine whether the Arg-to-Glu substitutions had an effect on heparin binding, each of the three mutants (along with wild-type human Neublastin) was subjected to Heparin Sepharose chromatography (FIG. 2B). Binding and elution conditions were similar to those used for cationic chromatography. However, the observed elution profile was significantly different from the cationic resin elution profile. Wild-type Neublastin eluted at approximately 720 mM sodium chloride (FIG. 2B; Peak H) whereas Arg51E, Arg49E, and Arg48E eluted at 570 mM (FIG. 2B; Peak G), 510 mM (FIG. 2B; Peak F), and 450 mM (FIG. 2B; Peak E) sodium chloride, respectively. Arg48E appeared to have a particularly dramatic effect on heparin binding. Taken together, these chromatography profiles suggested that each mutation decreases Neublastin's apparent affinity for heparin.

Example 3

Anionic Chromatography

At standard pH conditions of 6.5 and a sodium chloride concentration of 150 mM, Neublastin does not bind to anionic resins. In contrast, heparin sulfate does bind to anionic resins under these same conditions.

Figure 3A:
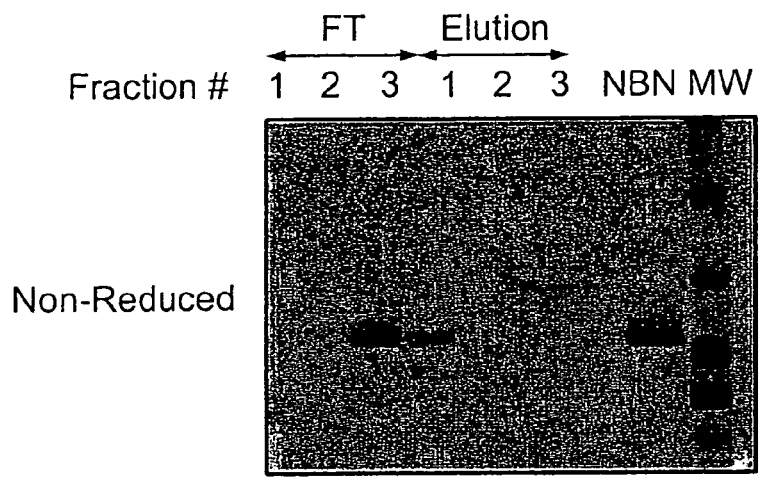
FIGS. 3A-3B are photographs depicting SDS/PAGE of wild-type Neublastin following anionic chromatography in the presence (2A) or absence (2 B) of heparin.
Figure 3B:
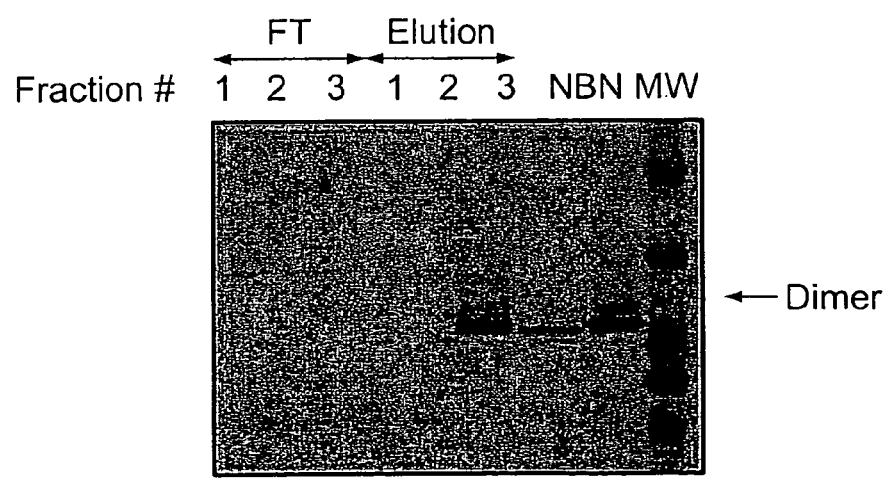

When Neublastin was pre-mixed in a 1:1 molar ratio with 16-kDa-heparin sulfate and applied to an anionic matrix using the above conditions, Neublastin bound and eluted with 600 mM sodium chloride (FIG. 3B, lanes marked "FT"), suggesting that Neublastin was binding the anionic matrix through its interaction with heparin sulfate. In the absence of heparin, Neublastin did not bind to the anionic resin (FIG. 3A, lanes marked "FT") and no Neublastin eluted with 600 mM sodium chloride (FIG. 3A, lanes marked "Elution"). These data provide further evidence of Neublastin's ability to bind to heparin.

Example 4

Chinese Hamster Ovary Cell Binding Studies

Neublastin has been shown previously to bind non-specifically to the surface of Chinese Hamster Ovary (CHO) cells. A Neublastin CHO cell-binding assay was established to determine whether this interaction is mediated, at least in part, through Neublastin's binding to cell surface heparin sulfate molecules.

Figure 4:
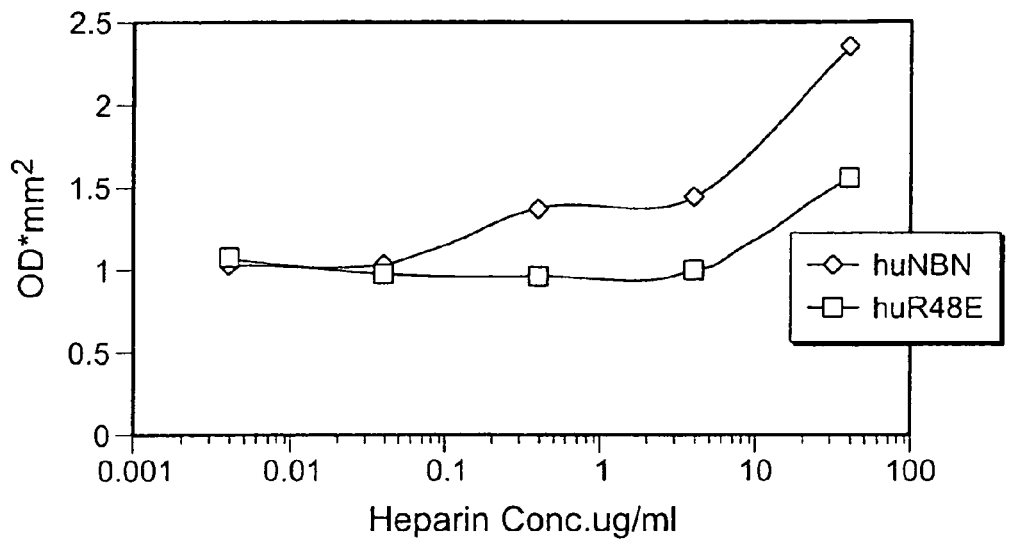
FIG. 4 is a graph depicting the results of a Neublastin CHO cell binding assay. Following SDS/PAGE and desitometry, OD values of Neublastin wild type and Arg48E mutant bands were plotted against the heparin concentration in each sample.

Wild-type human Neublastin (40 ug) or the Arg48E mutant was pre-mixed with CHO cells ($10^6$ cells) at a cell density which completely binds both Neublastin forms along with increasing amounts of 16 kDa heparin sulfate and incubated at 37° C. for 4 hours. Following incubation, the cells were pelleted by centrifugation and remaining non-bound Neublastin in the supernatant was subjected to SDS/PAGE analysis. After quantification of each protein band by densitometry, the resulting optical density value was plotted against the heparin concentration in each sample (FIG. 4).

At the two lower heparin concentrations, both the wild type and the mutant Neublastin forms had equal amounts of protein identified in the supernatant. However, as the heparin concentration increased to 0.5 ug/ml and higher, more wild-type Neublastin was identified in the supernatant than that of the Arg48E mutant. This observation suggested that heparin can compete with cell surface-bound heparin for wild-type Neublastin binding (i.e., binding of heparin to wild-type Neublastin results in its removal from the cell surface), whereas heparin cannot as readily compete off the Arg48E mutant. At the highest heparin concentration (50 ug/ml), the Arg48E mutant began to elute off the cell surface, suggesting an ionic interaction between heparin and the Arg48E mutant might be responsible for this observation.

Example 5

Heparin Binding of Wild Type Neublastin and Variant Neublastin Polypeptides

To further investigate the role of the identified arginine triad as a heparin-binding site of Neublastin, a heparin binding ELISA was established. In brief, an anti-Neublastin monoclonal antibody was coated onto a 96-well plate, followed by washing and the addition of one of the Neublastin forms. Biotinylated heparin was then added to the plate. Following an additional wash step, the Neublastin/Heparin complex was identified using a Strepavidin-HRP conjugate with a chemiluminescent substrate. This heparin-binding ELISA was used to compare wild type human Neublastin 113 amino acid (SEQ ID NO:1) and 104 amino acid (amino acids 10-113 of SEQ ID NO:1) forms to variant Neublastin polypeptides containing a single amino acid substitution (Arg48E, Arg49E, and Arg51E; SEQ ID NOS:2-4) as well as a double substitution (Arg48, 49E; SEQ ID NO:5).

Figure 5:
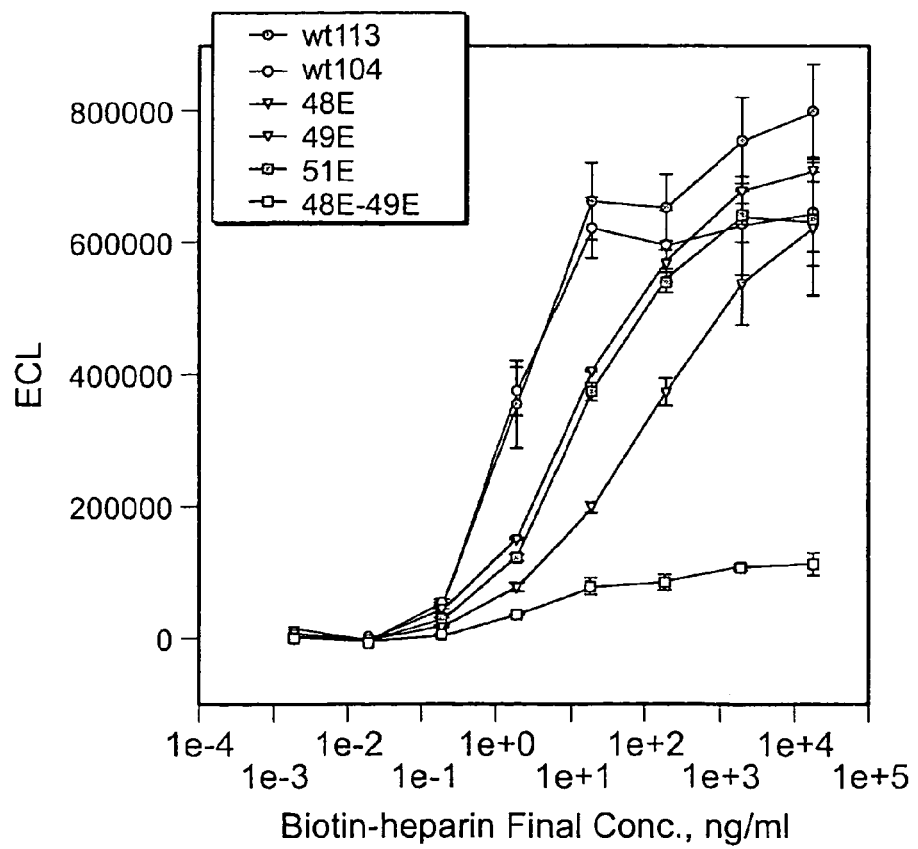
FIG. 5 is a graph depicting the results of a heparin binding ELISA using wild type human NBN113, wild type human NBN104, Arg48E, Arg49E, Arg51E, and Arg48, 49E.

Both wild-type forms of Neublastin bound heparin with an EC50 of ~1 ng/ml heparin (FIG. 5). Arg49E and Arg51E bound less efficiently, with an apparent EC50 of ~10 ng/ml, but maximum binding remained the same (FIG. 5). Of the three single point mutations, Arg48E had the most dramatic effect on heparin binding, with an apparent EC50 of ~100 ng/ml, but still achieved the same maximum heparin binding value when compared to the unmodified Neublastin forms (FIG. 5). The Arg48E mutant was thus one hundred fold less efficient in binding heparin as compared to the unmodified Neublastin forms and ten fold less efficient as compared to the other single substitution mutants. When both Arg48 and Arg49 were substituted with glutamate, heparin binding was almost eliminated, resulting in a seven-fold decrease in maximum heparin binding, but the EC50 remained within range of the single point mutants. These results suggest that Arg48 plays an important role in heparin binding due to its central location in the putative heparin-binding site.

Example 6

Kinase Receptor Activation Analysis of Wild-Type Neublastin and Heparin Binding Mutants To determine whether heparin-binding site mutations have an effect on Neublastin receptor signaling in a cell-based bioassay, mutant Neublastin forms along with the wild-type Neublastin were subjected to Kinase Receptor Activation (KIRA) analysis.

Figure 6:
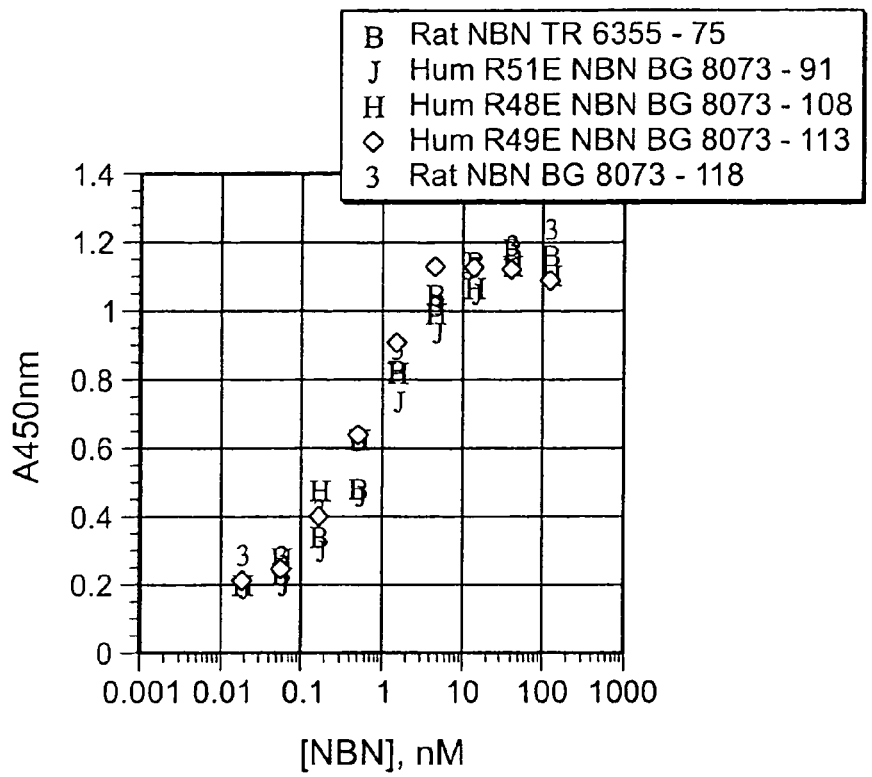
FIG. 6 is a graph depicting the results of KIRA analysis of wild type rat NBN113, Arg51E, Arg48E, Arg49E, and rat NBN113.

Each of the single Arg-to-Glu substitution mutants appeared identical to the unmodified control with respect to KIRA activity, suggesting that these mutants are structurally similar to the wild-type and are capable of activating the Neublastin receptor and signaling cascade (FIG. 6). Furthermore, these data suggest that heparin binding to Neublastin may not be required for receptor activation.

Figure 7A:
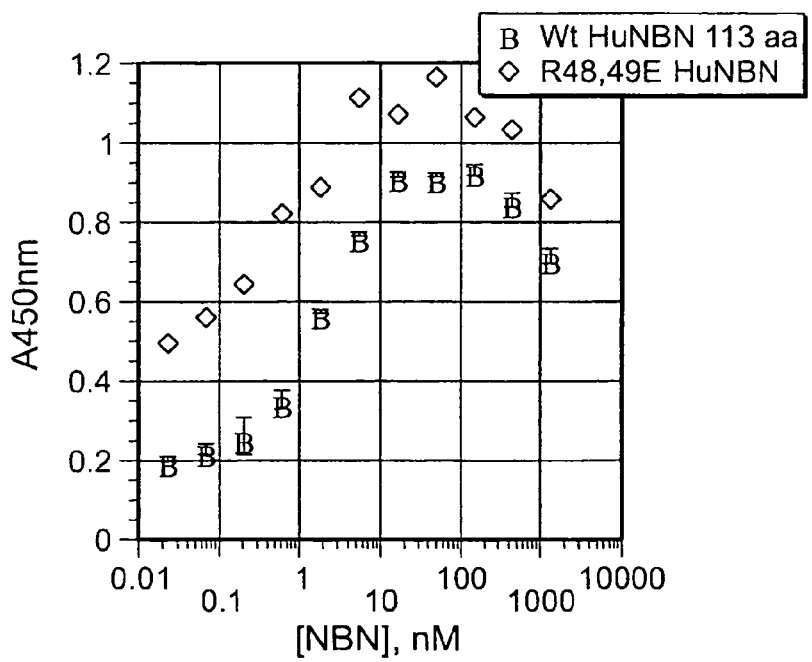
FIG. 7A is a graph depicting the results of KIRA analysis of wild type human Neublastin and Arg48,49E mutant human Neublastin (113 amino acid form).
Figure 7B:
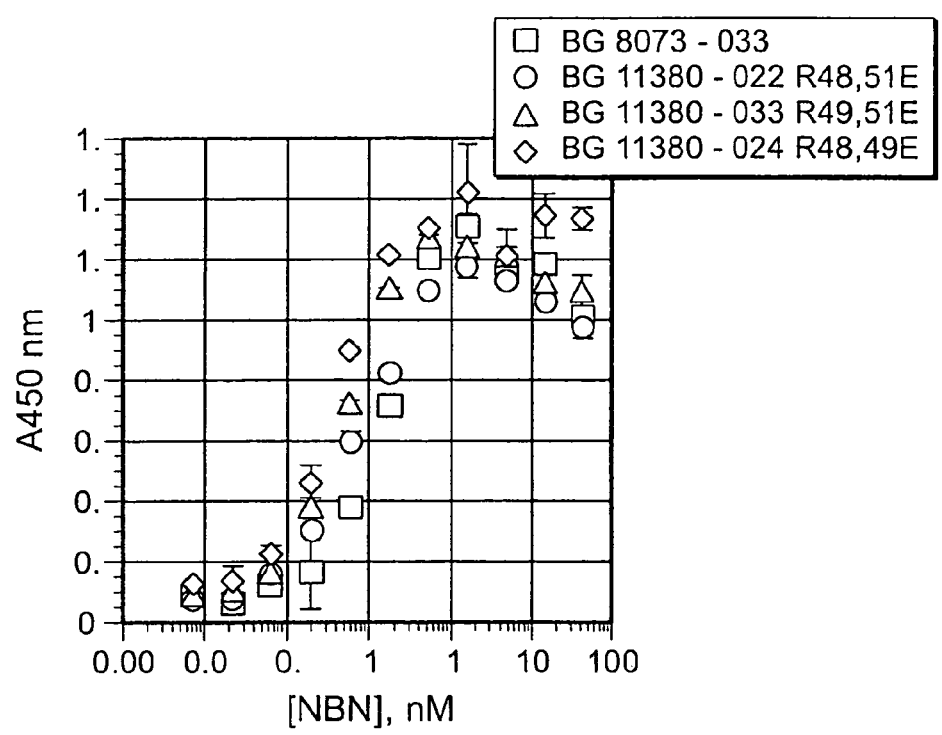
FIG. 7B is a graph depicting the results of KIRA analysis of wild type human Neublastin, Arg48,49E mutant human Neublastin (104 amino acid form), Arg48,51E human Neublastin (113 amino acid form), and Arg49,51E human Neublastin (113 amino acid form).

When the Arg48,49E double mutant (SEQ ID NO:5; 113 amino acid form) was subjected to KIRA analysis, its apparent EC50 was shifted to the left by approximately one order of magnitude with an increase in its maximum receptor activation when compared with the wild-type human Neublastin control (FIG. 7A). Similarly, the Arg48,49E double mutant (SEQ ID NO:7; 104 amino acid form) also exhibited increased potency as compared to wild-type Neublastin (FIG. 7B). Each of the Arg48,51E and Arg49,51E double mutants (SEQ ID NO:9 and SEQ ID NO:8, respectively; 113 amino acid forms) appeared similar to the unmodified Neublastin control with respect to KIRA activity (FIG. 7B).

Example 7

Ternary Complex Analysis

Figure 8:
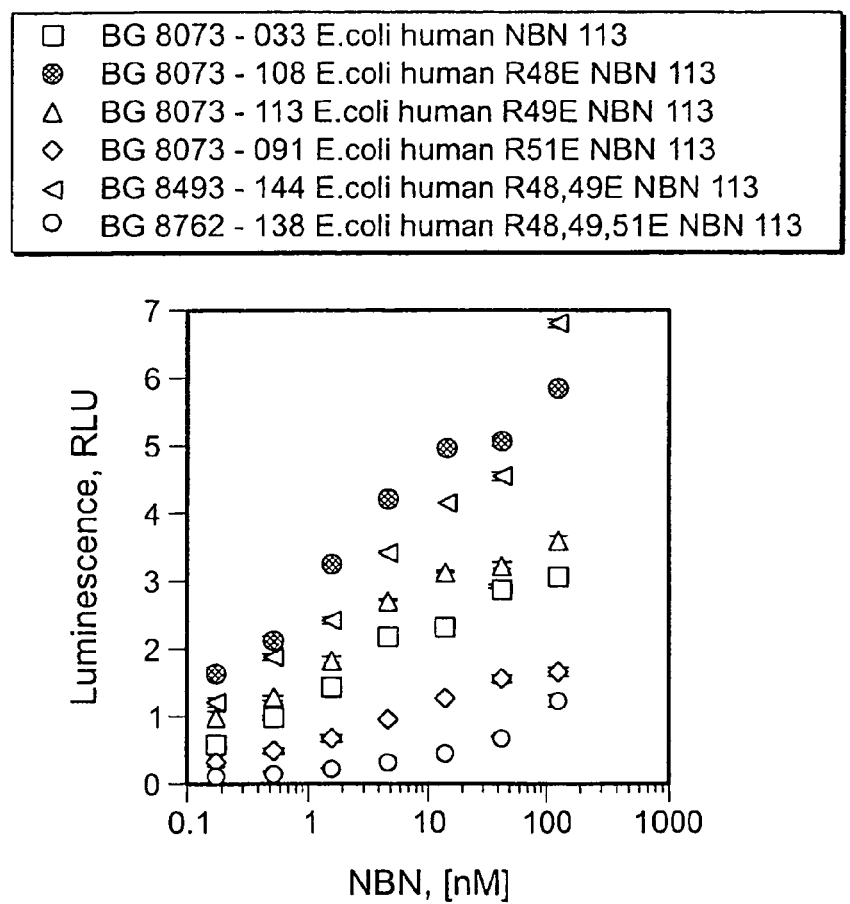
FIG. 8 is a graph depicting the results of ternary complex analysis of wild type human Neublastin, Arg48E, Arg49E, Arg51E, Arg48,49E, and Arg48,49,51E Neublastin forms.

Wild-type human Neublastin and each of the heparin mutants were subjected to ternary complex analysis using two slightly different protocols. The first protocol combined Neublastin's receptor components (GFRalpha3 and RET) along with Neublastin in a pool before addition to an ELISA plate coated with capture antibody (FIG. 8). The second protocol added these components sequentially to an ELISA plate with GFRalpha3 added first, followed by Neublastin, and then RET (FIG. 9).

When the components were added together as a pool, maximum binding was achieved with both Arg48E and Arg48,49E, suggesting that these Neublastin forms have the highest affinity for their receptor. Wild-type Neublastin appeared to bind with a similar affinity to that of the Arg49E mutant, whereas the Arg51E and a triple mutant (Arg48, 49 and 51 all substituted to glutamate) demonstrated the weakest receptor binding.

When the receptor components were added sequentially, Arg48E showed the best receptor binding. However under these conditions, the double mutant weakly bound to its receptor with an affinity that appeared similar to the Arg51E mutant. Arg49E and wild-type Neublastin had an affinity for the receptor that was midway between the observed maximum and minimum binding. The triple mutant did not bind under these conditions. Overall, these data suggest that Arg48 plays a pivotal role in affecting Neublastin's affinity for its receptor.

Example 8

Near and Far UV CD Analysis

To further investigate the effects of the double mutations on Neublastin's secondary and tertiary structure, the Arg48,49E double mutant was subjected to both Near and Far UV CD analysis. Although subtle differences were detected in the secondary and tertiary structures, the conformation of the double mutant was very close to that of the wild-type Neublastin.

Example 9

Pharmacokinetic Analysis of the Neublastin Arg48, 49E Double Mutant

Human Neublastin exhibits poor pharmacokinetics (PK) when administered to rats intravenously (IV) or subcutaneously (SC), with an overall bioavailability of less than 1%. Heparin-based clearance may be one of the reasons for this low bioavailability. To determine whether heparin-based clearance participates in human Neublastin's rapid clearance from the rat, the Arg48,49E double mutant (along with the wild-type control) was subjected to PK analysis.

Figure 10:
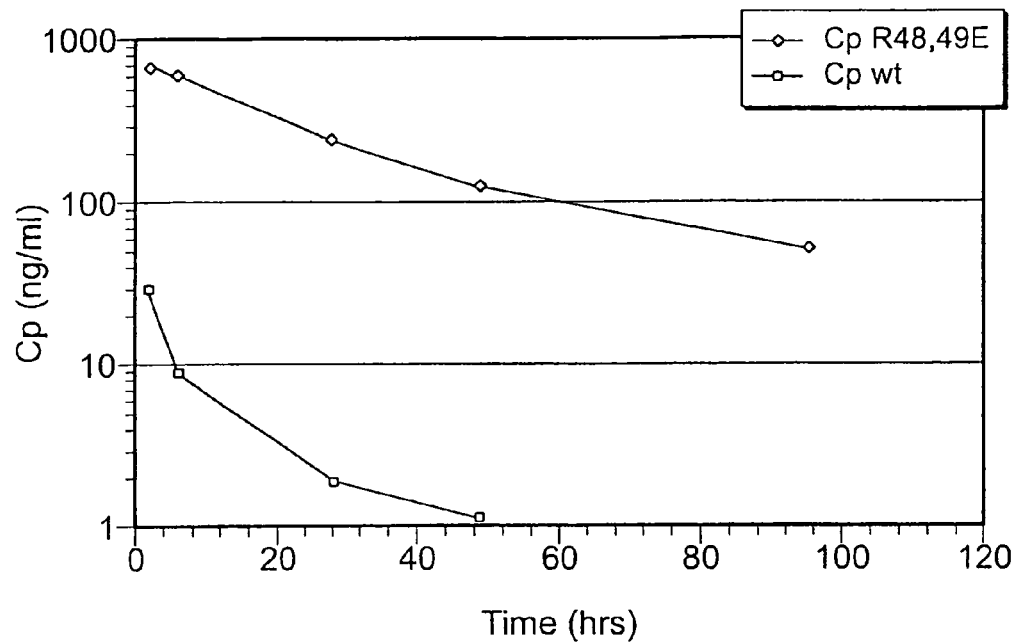
FIG. 10 is a graph depicting the results of pharmacokinetics analysis of wild type Neublastin and Arg48,49E following a single bolus 7 mg/kg subcutaneous injection (Neublastin plasma concentrations were determined using the Neublastin detection ELISA).

Both forms were administered separately in rats at 7 mg/kg SC. Serum samples were collected starting at 1 hour, completed at 96 hours, and analyzed for Neublastin (FIG. 10). The observed area under the curve (AUC) for wild-type Neublastin was ~109 whereas the observed AUC for the double mutant was 20,145. This represented a 185-fold increase in AUC for the double mutant (compared to wild-type Neublastin) and a significant increase in serum exposure.

Figure 11:
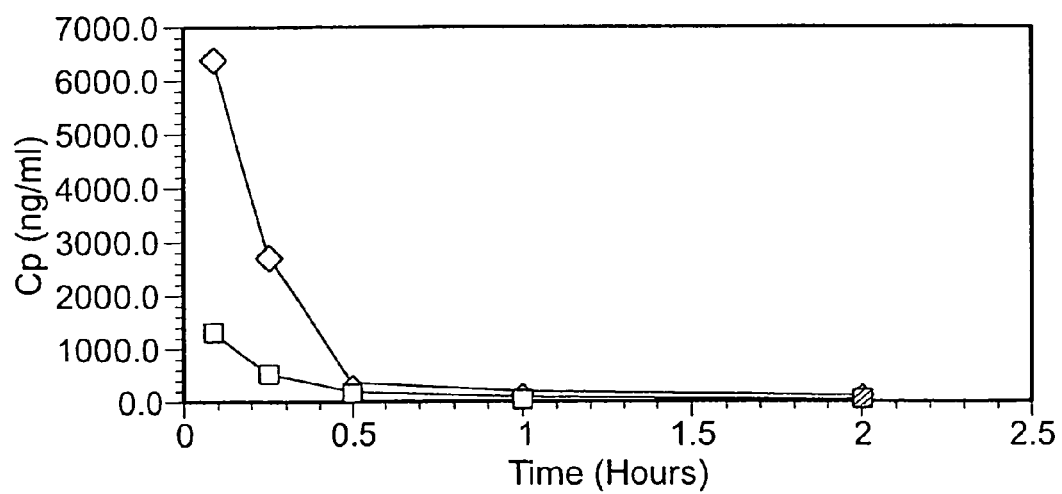
FIG. 11 is a graph depicting the results of pharmacokinetics analysis of wild type Neublastin and Arg48,49E following a single bolus 1 mg/kg intravenous injection (Neublastin plasma concentrations were determined using the Neublastin detection ELISA).

Both the wild type and double mutant Neublastin were also subjected to PK analysis following IV administration (1 mg/kg). The initial plasma concentration of the double mutant was approximately six-fold higher (diamonds) than that of the wild-type control (squares) at five minutes following injection but quickly approached wild type levels within one hour (FIG. 11). These data suggest that the double mutation in Neublastin aids in increasing serum exposure but does not affect the overall clearance rate.

Taken together with the SC observation, heparin-binding appears to be especially relevant following SC administration, perhaps resulting in a depot-like effect. Once Neublastin enters circulation, the rate at which the double mutant and wild type molecules are cleared is approximately the same.

To address the rate at which Neublastin is cleared from circulation in the rat, both the wild type and double mutant forms of Neublastin were PEGylated with 10 kDa PEG using SPA-based coupling chemistry. Since Neublastin is a homodimer with no native lysine residues, the 10-kDa moieties specifically labeled the amino terminus of each monomer. 2×10K PEGylated human double mutant neublastin was purified to homogeneity, and subjected to structural and biological analysis prior to PK analysis.

Figure 12:
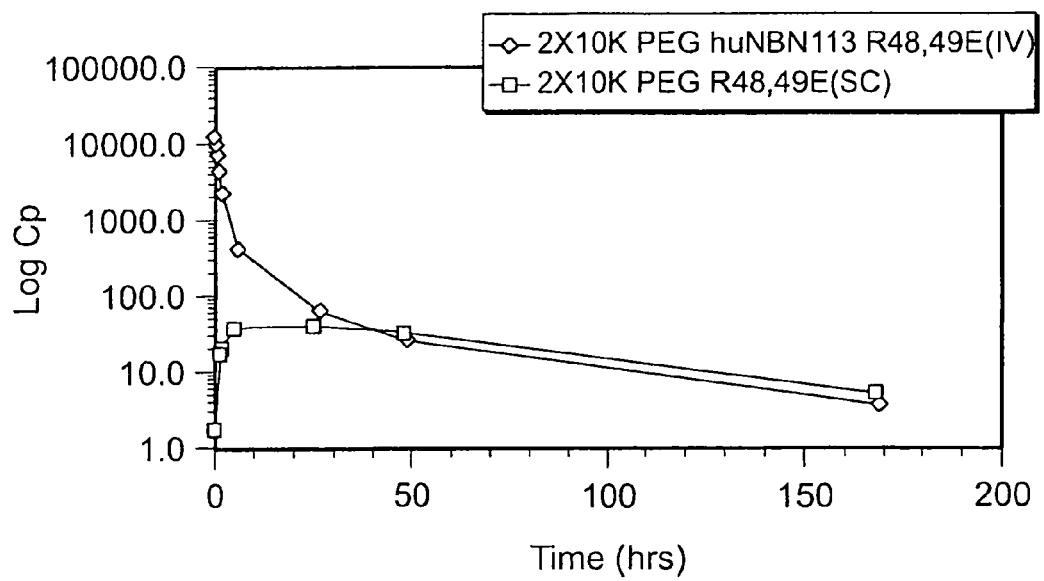
FIG. 12 is a graph depicting the results of pharmacokinetics analysis of 2×10K PEGylated Arg48,49E Neublastin following a single bolus subcutaneous 7 mg/kg (data presented are extrapolated down to 1 mg/kg) injection and 2×10K PEGylated Arg48,49E Neublastin administered intravenously at 1 mg/kg (Neublastin plasma concentrations were determined using the Neublastin detection ELISA).

2×10K PEG Arg48, 49E double mutant was injected either IV (1 mg/kg) or SC (7 mg/kg) into rats and serum collected at various time points for analysis. Following IV administration, 2×10K PEG double mutant achieved the theoretical Cmax of 10 ug/ml (diamonds) with typical alpha and beta phases (FIG. 12). SC administration of the PEGylated double mutant demonstrated a Cmax of 40 ng/ml at 24 hours injection (FIG. 12). Once the drug reached circulation, the apparent rate of clearance paralleled that of IV dose. Bioavailability of this construct was approximately 10% compared to less than 1% for the non-PEGylated or PEGylated wild type human Neublastin.

Example 10

Expression of a Neublastin Heparin-Binding Mutant in Chinese Hamster Ovary Cells Plasmid constructs encoding wild type and mutant Neublastin were expressed in CHO cells and the amount of secreted soluble protein was measured by ELISA. The plasmid constructs used in these experiments encoded a fusion protein containing the human growth hormone signal peptide (SigPep) (with or without an intron included in the plasmid) fused to (i) the carboxy terminal 104 amino acids of wild type human Neublastin, or (ii) the Arg48,49E double mutant (104 amino acid form).

The following are the amino acid sequences of the Neublastin fusion proteins used in these experiments. The Neublastin sequences are in upper case type. The human growth hormone signal peptide sequences are in lower case type. The junction of the signal peptide and Neublastin sequences is indicated with a carat (^). The amino acids at positions 48 and 49 are underlined.

SigPep-NBN (wild type): matgsrtslllafgllclswlqeg-sa^AAAGARGCRLRSQLVPVRALGLGHRS-DELVRFRFCSGSCRRARSPHDLSLAS-LLGAGALRPPPGSRPVSQPCCRPTR-YEAVSFMDVNSTWRTVDRLSATACGCLG (SEQ ID NO:13).

SigPep-NBN (Arg48,49E): matgsrtslllafgllclswlqeg-sa^AAAGARGCRLRSQLVPVRALGLGHRS-DELVRFRFCSGSCEEARSPHDLSLASLLGAG-ALRPPPGSRPVSQPCCRPTRYEAVSFMD-VNSTWRTVDRLSATACGCLG (SEQ ID NO:14).

CHO cells were transfected with plasmids encoding each of the foregoing forms of Neublastin and cultured in 384-well plates. After several weeks, wells that contained growing cells were transferred to fresh 96-well culture plates. Conditioned medium was analyzed by ELISA to measure the titer of soluble Neublastin. The cumulative absorbance data for each plasmid tested (mean value with one standard deviation as error bars) was detected.

Figure 13:
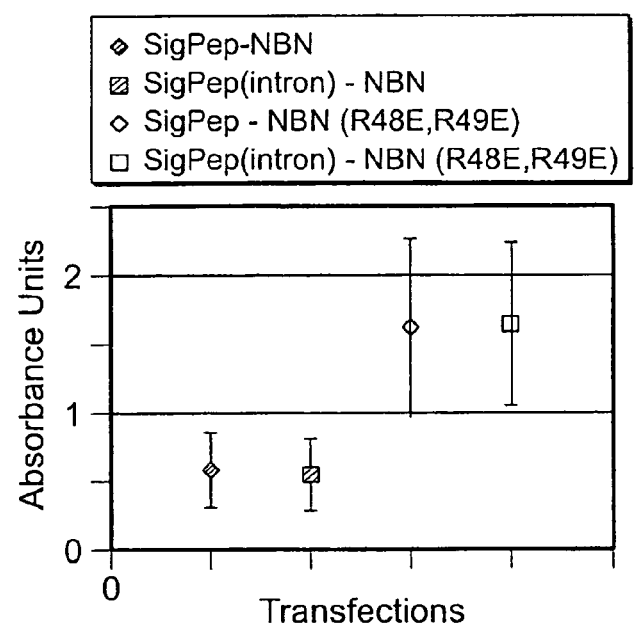
FIG. 13 is a graph depicting relative Neublastin expression levels in CHO cells transfected with plasmids encoding wild type Neublastin or Arg48,49E.

Transfection of CHO cells with plasmids encoding the Arg48,49E double mutant resulted in a significantly increased number of cell lines exhibiting high expression levels of recombinant protein, as compared to cells transfected with plasmids encoding wild type Neublastin (FIG. 13).

Figure 14:
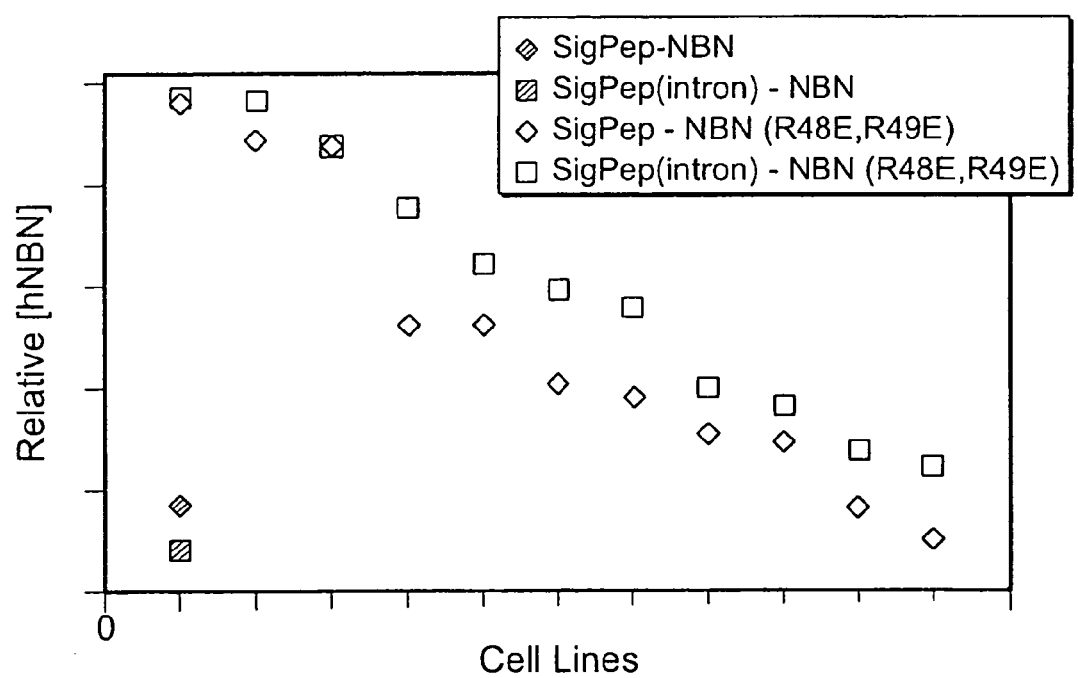
FIG. 14 is a graph depicting relative Neublastin expression levels in the leading Arg48,49E double mutant transfected CHO cell lines and a leading wild type Neublastin transfected CHO cell line.

The leading cell lines from each transfection were further expanded. Fixed numbers of cells were cultured for three days and total cell count, viability, and titer were determined. The titers of Neublastin expressed from the leading Arg48, 49E double mutant cell lines were roughly five-fold greater than those of a leading wild type Neublastin cell line (FIG. 14).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising an amino acid sequence that is at least 80% identical to amino acids 15-113 of SEQ ID NO:1, wherein the amino acid sequence comprises an amino acid other than arginine substituted at the positions corresponding to position 48 and position 49 of SEQ ID NO:1, wherein the polypeptide, when dimerized, binds to a complex containing GFRalpha3 and RET.

2. The polypeptide of claim 1, wherein the arginine residue at the position corresponding to position 48 of SEQ ID NO:1 is substituted with a non-conservative amino acid residue.

3. The polypeptide of claim 1, wherein the arginine residue at the position corresponding to position 48 of SEQ ID NO:1 is substituted with glutamic acid.

4. The polypeptide of claim 1, wherein the arginine residue at the position corresponding to position 49 of SEQ ID NO:1 is substituted with a non-conservative amino acid residue.

5. The polypeptide of claim 1, wherein the arginine residue at the position corresponding to position 49 of SEQ ID NO:1 is substituted with glutamic acid.

6. The polypeptide of claim 1, wherein the arginine residue at the position corresponding to position 48 of SEQ ID NO:1 and the arginine residue at the position corresponding to position 49 of SEQ ID NO:1 are substituted with non-conservative amino acid residues.

7. The polypeptide of claim 1, wherein the arginine residue at the position corresponding to position 48 of SEQ ID NO:1 and the arginine residue at the position corresponding to position 49 of SEQ ID NO:1 are each substituted with glutamic acid.

8. The polypeptide of claim 1, wherein the amino acid sequence is at least 90% identical to amino acids 15-113 of SEQ ID NO:1.

9. The polypeptide of claim 1, wherein the amino acid sequence is at least 95% identical to amino acids 15-113 of SEQ ID NO:1.

10. A polypeptide comprising amino acids 15-113 of SEQ ID NO:5.

11. The polypeptide of claim 10, wherein the polypeptide comprises amino acids 10-113 of SEQ ID NO:5.

12. The polypeptide of claim 10, wherein the polypeptide comprises the amino acid sequence of SEQ ID NO:5.

13. The polypeptide of claim 6, wherein the amino acid sequence is at least 90% identical to amino acids 15-113 of SEQ ID NO:1.

14. The polypeptide of claim 6, wherein the amino acid sequence is at least 95% identical to amino acids 15-113 of SEQ ID NO:1.

15. The polypeptide of claim 7, wherein the amino acid sequence is at least 90% identical to amino acids 15-113 of SEQ ID NO:1.

16. The polypeptide of claim 7, wherein the amino acid sequence is at least 95% identical to amino acids 15-113 of SEQ ID NO:1.

17. A polypeptide consisting of amino acids 15-113 of SEQ ID NO:5.

18. A polypeptide consisting of amino acids 10-113 of SEQ ID NO:5.

19. A polypeptide consisting of the amino acid sequence of SEQ ID NO:5.

20. A conjugate comprising the polypeptide of claim 1 conjugated to a non-naturally occurring polymer.

21. The conjugate of claim 20, wherein the non-naturally occurring polymer is a polyalkylene glycol.

22. The conjugate of claim 21, wherein the polyalkylene glycol is polyethylene glycol.

23. The conjugate of claim 22, wherein the polyethylene glycol is coupled to the polypeptide at the amino terminus.

24. The conjugate of claim 22, wherein the polyethylene glycol is coupled to the polypeptide at an internal polymer conjugation site.

25. A conjugate comprising the polypeptide of claim 8 conjugated to a non-naturally occurring polymer.

26. The conjugate of claim 25, wherein the non-naturally occurring polymer is a polyalkylene glycol.

27. The conjugate of claim 26, wherein the polyalkylene glycol is polyethylene glycol.

28. The conjugate of claim 27, wherein the polyethylene glycol is coupled to the polypeptide at the amino terminus.

29. The conjugate of claim 27, wherein the polyethylene glycol is coupled to the polypeptide at an internal polymer conjugation site.

30. A conjugate comprising the polypeptide of claim 9 conjugated to a non-naturally occurring polymer.

31. The conjugate of claim 30, wherein the non-naturally occurring polymer is a polyalkylene glycol.

32. The conjugate of claim 31, wherein the polyalkylene glycol is polyethylene glycol.

33. The conjugate of claim 32, wherein the polyethylene glycol is coupled to the polypeptide at the amino terminus.

34. The conjugate of claim 32, wherein the polyethylene glycol is coupled to the polypeptide at an internal polymer conjugation site.

35. A conjugate comprising the polypeptide of claim 10 conjugated to a non-naturally occurring polymer.

36. The conjugate of claim 35, wherein the non-naturally occurring polymer is a polyalkylene glycol.

37. The conjugate of claim 36, wherein the polyalkylene glycol is polyethylene glycol.

38. The conjugate of claim 37, wherein the polyethylene glycol is coupled to the polypeptide at the amino terminus.

39. The conjugate of claim 37, wherein the polyethylene glycol is coupled to the polypeptide at an internal polymer conjugation site.

40. A conjugate comprising the polypeptide of claim 11 conjugated to a non-naturally occurring polymer.

41. The conjugate of claim 40, wherein the non-naturally occurring polymer is a polyalkylene glycol.

42. The conjugate of claim 41, wherein the polyalkylene glycol is polyethylene glycol.

43. The conjugate of claim 42, wherein the polyethylene glycol is coupled to the polypeptide at the amino terminus.

44. The conjugate of claim 42, wherein the polyethylene glycol is coupled to the polypeptide at an internal polymer conjugation site.

45. A conjugate comprising the polypeptide of claim 18 conjugated to a non-naturally occurring polymer.

46. The conjugate of claim 45, wherein the non-naturally occurring polymer is a polyalkylene glycol.

47. The conjugate of claim 46, wherein the polyalkylene glycol is polyethylene glycol.

48. The conjugate of claim 47, wherein the polyethylene glycol is coupled to the polypeptide at the amino terminus.

49. The conjugate of claim 47, wherein the polyethylene glycol is coupled to the polypeptide at an internal polymer conjugation site.

50. A conjugate comprising the polypeptide of claim 19 conjugated to a non-naturally occurring polymer.

51. The conjugate of claim 50, wherein the non-naturally occurring polymer is a polyalkylene glycol.

52. The conjugate of claim 51, wherein the polyalkylene glycol is polyethylene glycol.

53. The conjugate of claim 52, wherein the polyethylene glycol is coupled to the polypeptide at the amino terminus.

54. The conjugate of claim 52, wherein the polyethylene glycol is coupled to the polypeptide at an internal polymer conjugation site.

55. A fusion protein comprising the polypeptide of claim 1 and a heterologous amino acid sequence.

56. A fusion protein comprising the polypeptide of claim 8 and a heterologous amino acid sequence.

57. A fusion protein comprising the polypeptide of claim 9 and a heterologous amino acid sequence.

58. A fusion protein comprising the polypeptide of claim 10 and a heterologous amino acid sequence.

59. A fusion protein comprising the polypeptide of claim 11 and a heterologous amino acid sequence.

60. A fusion protein comprising the polypeptide of claim 18 and a heterologous amino acid sequence.

61. A fusion protein comprising the polypeptide of claim 19 and a heterologous amino acid sequence.

62. A dimer comprising two polypeptides according to claim 1.

63. A dimer comprising two polypeptides according to claim 8.

64. A dimer comprising two polypeptides according to claim 9.

65. A dimer comprising two polypeptides according to claim 10.

66. A dimer comprising two polypeptides according to claim 11.

67. A dimer comprising two polypeptides according to claim 18.

68. A dimer comprising two polypeptides according to claim 19.

69. A dimer comprising two conjugates according to claim 42.

70. A dimer comprising two conjugates according to claim 43.

71. A dimer comprising two conjugates according to claim 52.

72. A dimer comprising two conjugates according to claim 53.

73. A pharmaceutical composition comprising the polypeptide of claim 1 and a pharmaceutically acceptable carrier or excipient.

74. A pharmaceutical composition comprising the polypeptide of claim 8 and a pharmaceutically acceptable carrier or excipient.

75. A pharmaceutical composition comprising the polypeptide of claim 9 and a pharmaceutically acceptable carrier or excipient.

76. A pharmaceutical composition comprising the polypeptide of claim 10 and a pharmaceutically acceptable carrier or excipient.

77. A pharmaceutical composition comprising the polypeptide of claim 11 and a pharmaceutically acceptable carrier or excipient.

78. A pharmaceutical composition comprising the polypeptide of claim 18 and a pharmaceutically acceptable carrier or excipient.

79. A pharmaceutical composition comprising the polypeptide of claim 19 and a pharmaceutically acceptable carrier or excipient.

80. A pharmaceutical composition comprising the conjugate of claim 42 and a pharmaceutically acceptable carrier or excipient.

81. A pharmaceutical composition comprising the conjugate of claim 43 and a pharmaceutically acceptable carrier or excipient.

82. A pharmaceutical composition comprising the conjugate of claim 52 and a pharmaceutically acceptable carrier or excipient.

83. A pharmaceutical composition comprising the conjugate of claim 53 and a pharmaceutically acceptable carrier or excipient.

84. A pharmaceutical composition comprising the dimer of claim 66 and a pharmaceutically acceptable carrier or excipient.

85. A pharmaceutical composition comprising the dimer of claim 68 and a pharmaceutically acceptable carrier or excipient.

86. A pharmaceutical composition comprising the dimer of claim 69 and a pharmaceutically acceptable carrier or excipient.

87. A pharmaceutical composition comprising the dimer of claim 70 and a pharmaceutically acceptable carrier or excipient.

88. A pharmaceutical composition comprising the dimer of claim 71 and a pharmaceutically acceptable carrier or excipient.

89. A pharmaceutical composition comprising the dimer of claim 72 and a pharmaceutically acceptable carrier or excipient.

90. A method of treating a peripheral neuropathy, the method comprising administering to a human in need of such treatment a therapeutically effective amount of the pharmaceutical composition of claim 73.

91. A method of treating neuropathic pain, the method comprising administering to a human in need of such treatment a therapeutically effective amount of the pharmaceutical composition of claim 73.

92. The method of claim 91, wherein the neuropathic pain is associated with post-herpetic neuralgia.

93. The method of claim 91, wherein the neuropathic pain is associated with sciatica.

94. A method of treating painful diabetic neuropathy, the method comprising administering to a human in need of such treatment a therapeutically effective amount of the pharmaceutical composition of claim 73.

95. A method of activating the RET receptor in a human, the method comprising administering to the human an effective amount of the pharmaceutical composition of claim 73.

96. A method of treating a peripheral neuropathy, the method comprising administering to a human in need of such treatment a therapeutically effective amount of the pharmaceutical composition of claim 74.

97. A method of treating neuropathic pain, the method comprising administering to a human in need of such treatment a therapeutically effective amount of the pharmaceutical composition of claim 74.

98. The method of claim 97, wherein the neuropathic pain is associated with post-herpetic neuralgia.

99. The method of claim 97, wherein the neuropathic pain is associated with sciatica.

100. A method of treating painful diabetic neuropathy, the method comprising administering to a human in need of such treatment a therapeutically effective amount of the pharmaceutical composition of claim 74.

101. A method of activating the RET receptor in a human, the method comprising administering to the human an effective amount of the pharmaceutical composition of claim 74.

102. A method of treating a peripheral neuropathy, the method comprising administering to a human in need of such treatment a therapeutically effective amount of the pharmaceutical composition of claim 75.

103. A method of treating neuropathic pain, the method comprising administering to a human in need of such treatment a therapeutically effective amount of the pharmaceutical composition of claim 75.

104. The method of claim 103, wherein the neuropathic pain is associated with post-herpetic neuralgia.

105. The method of claim 103, wherein the neuropathic pain is associated with sciatica.

106. A method of treating painful diabetic neuropathy, the method comprising administering to a human in need of such treatment a therapeutically effective amount of the pharmaceutical composition of claim 75.

107. A method of activating the RET receptor in a human, the method comprising administering to the human an effective amount of the pharmaceutical composition of claim 75.

108. A method of treating a peripheral neuropathy, the method comprising administering to a human in need of such treatment a therapeutically effective amount of the pharmaceutical composition of claim 76.

109. A method of treating neuropathic pain, the method comprising administering to a human in need of such treatment a therapeutically effective amount of the pharmaceutical composition of claim 76.

110. The method of claim 109, wherein the neuropathic pain is associated with post-herpetic neuralgia.

111. The method of claim 109, wherein the neuropathic pain is associated with sciatica.

112. A method of treating painful diabetic neuropathy, the method comprising administering to a human in need of such treatment a therapeutically effective amount of the pharmaceutical composition of claim 76.

113. A method of activating the RET receptor in a human, the method comprising administering to the human an effective amount of the pharmaceutical composition of claim 76.

114. A method of treating a peripheral neuropathy, the method comprising administering to a human in need of such treatment a therapeutically effective amount of the pharmaceutical composition of claim 77.

115. A method of treating neuropathic pain, the method comprising administering to a human in need of such treatment a therapeutically effective amount of the pharmaceutical composition of claim 77.

116. The method of claim 115, wherein the neuropathic pain is associated with post-herpetic neuralgia.

117. The method of claim 115, wherein the neuropathic pain is associated with sciatica.

118. A method of treating painful diabetic neuropathy, the method comprising administering to a human in need of such treatment a therapeutically effective amount of the pharmaceutical composition of claim 77.

119. A method of activating the RET receptor in a human, the method comprising administering to the human an effective amount of the pharmaceutical composition of claim 77.

120. A method of treating a peripheral neuropathy, the method comprising administering to a human in need of such treatment a therapeutically effective amount of the pharmaceutical composition of claim 78.

121. A method of treating neuropathic pain, the method comprising administering to a human in need of such treatment a therapeutically effective amount of the pharmaceutical composition of claim 78.

122. The method of claim 121, wherein the neuropathic pain is associated with post-herpetic neuralgia.

123. The method of claim 121, wherein the neuropathic pain is associated with sciatica.

124. A method of treating painful diabetic neuropathy, the method comprising administering to a human in need of such treatment a therapeutically effective amount of the pharmaceutical composition of claim 78.

125. A method of activating the RET receptor in a human, the method comprising administering to the human an effective amount of the pharmaceutical composition of claim 78.

126. A method of treating a peripheral neuropathy, the method comprising administering to a human in need of such treatment a therapeutically effective amount of the pharmaceutical composition of claim 79.

127. A method of treating neuropathic pain, the method comprising administering to a human in need of such treatment a therapeutically effective amount of the pharmaceutical composition of claim 79.

128. The method of claim 127, wherein the neuropathic pain is associated with post-herpetic neuralgia.

129. The method of claim 127, wherein the neuropathic pain is associated with sciatica.

130. A method of treating painful diabetic neuropathy, the method comprising administering to a human in need of such treatment a therapeutically effective amount of the pharmaceutical composition of claim 79.

131. A method of activating the RET receptor in a human, the method comprising administering to the human an effective amount of the pharmaceutical composition of claim 79.

132. A method of treating a peripheral neuropathy, the method comprising administering to a human in need of such treatment a therapeutically effective amount of the pharmaceutical composition of claim 80.

133. A method of treating neuropathic pain, the method comprising administering to a human in need of such treatment a therapeutically effective amount of the pharmaceutical composition of claim 80.

134. The method of claim 133, wherein the neuropathic pain is associated with post-herpetic neuralgia.

135. The method of claim 133, wherein the neuropathic pain is associated with sciatica.

136. A method of treating painful diabetic neuropathy, the method comprising administering to a human in need of such treatment a therapeutically effective amount of the pharmaceutical composition of claim 80.

137. A method of activating the RET receptor in a human, the method comprising administering to the human an effective amount of the pharmaceutical composition of claim 80.

138. A method of treating a peripheral neuropathy, the method comprising administering to a human in need of such treatment a therapeutically effective amount of the pharmaceutical composition of claim 81.

139. A method of treating neuropathic pain, the method comprising administering to a human in need of such treatment a therapeutically effective amount of the pharmaceutical composition of claim 81.

140. The method of claim 139, wherein the neuropathic pain is associated with post-herpetic neuralgia.

141. The method of claim 139, wherein the neuropathic pain is associated with sciatica.

142. A method of treating painful diabetic neuropathy, the method comprising administering to a human in need of such treatment a therapeutically effective amount of the pharmaceutical composition of claim 81.

143. A method of activating the RET receptor in a human, the method comprising administering to the human an effective amount of the pharmaceutical composition of claim 81.

144. A method of treating a peripheral neuropathy, the method comprising administering to a human in need of such treatment a therapeutically effective amount of the pharmaceutical composition of claim 82.

145. A method of treating neuropathic pain, the method comprising administering to a human in need of such treatment a therapeutically effective amount of the pharmaceutical composition of claim 82.

146. The method of claim 145, wherein the neuropathic pain is associated with post-herpetic neuralgia.

147. The method of claim 145, wherein the neuropathic pain is associated with sciatica.

148. A method of treating painful diabetic neuropathy, the method comprising administering to a human in need of such treatment a therapeutically effective amount of the pharmaceutical composition of claim 82.

149. A method of activating the RET receptor in a human, the method comprising administering to the human an effective amount of the pharmaceutical composition of claim 82.

150. A method of treating a peripheral neuropathy, the method comprising administering to a human in need of such treatment a therapeutically effective amount of the pharmaceutical composition of claim 83.

151. A method of treating neuropathic pain, the method comprising administering to a human in need of such treatment a therapeutically effective amount of the pharmaceutical composition of claim 83.

152. The method of claim 151, wherein the neuropathic pain is associated with post-herpetic neuralgia.

153. The method of claim 151, wherein the neuropathic pain is associated with sciatica.

154. A method of treating painful diabetic neuropathy, the method comprising administering to a human in need of such treatment a therapeutically effective amount of the pharmaceutical composition of claim 83.

155. A method of activating the RET receptor in a human, the method comprising administering to the human an effective amount of the pharmaceutical composition of claim 83.

156. A method of treating a peripheral neuropathy, the method comprising administering to a human in need of such treatment a therapeutically effective amount of the pharmaceutical composition of claim 84.

157. A method of treating neuropathic pain, the method comprising administering to a human in need of such treatment a therapeutically effective amount of the pharmaceutical composition of claim 84.

158. The method of claim 157, wherein the neuropathic pain is associated with post-herpetic neuralgia.

159. The method of claim 157, wherein the neuropathic pain is associated with sciatica.

160. A method of treating painful diabetic neuropathy, the method comprising administering to a human in need of such treatment a therapeutically effective amount of the pharmaceutical composition of claim 84.

161. A method of activating the RET receptor in a human, the method comprising administering to the human an effective amount of the pharmaceutical composition of claim 84.

162. A method of treating a peripheral neuropathy, the method comprising administering to a human in need of such treatment a therapeutically effective amount of the pharmaceutical composition of claim 85.

163. A method of treating neuropathic pain, the method comprising administering to a human in need of such treatment a therapeutically effective amount of the pharmaceutical composition of claim 85.

164. The method of claim 163, wherein the neuropathic pain is associated with post-herpetic neuralgia.

165. The method of claim 163, wherein the neuropathic pain is associated with sciatica.

166. A method of treating painful diabetic neuropathy, the method comprising administering to a human in need of such 166. [continued from previous page] treatment a therapeutically effective amount of the pharmaceutical composition of claim 85.

167. A method of activating the RET receptor in a human, the method comprising administering to the human an effective amount of the pharmaceutical composition of claim 85.

168. A method of treating a peripheral neuropathy, the method comprising administering to a human in need of such treatment a therapeutically effective amount of the pharmaceutical composition of claim 86.

169. A method of treating neuropathic pain, the method comprising administering to a human in need of such treatment a therapeutically effective amount of the pharmaceutical composition of claim 86.

170. The method of claim 169, wherein the neuropathic pain is associated with post-herpetic neuralgia.

171. The method of claim 169, wherein the neuropathic pain is associated with sciatica.

172. A method of treating painful diabetic neuropathy, the method comprising administering to a human in need of such treatment a therapeutically effective amount of the pharmaceutical composition of claim 86.

173. A method of activating the RET receptor in a human, the method comprising administering to the human an effective amount of the pharmaceutical composition of claim 86.

174. A method of treating a peripheral neuropathy, the method comprising administering to a human in need of such treatment a therapeutically effective amount of the pharmaceutical composition of claim 87.

175. A method of treating neuropathic pain, the method comprising administering to a human in need of such treatment a therapeutically effective amount of the pharmaceutical composition of claim 87.

176. The method of claim 175, wherein the neuropathic pain is associated with post-herpetic neuralgia.

177. The method of claim 175, wherein the neuropathic pain is associated with sciatica.

178. A method of treating painful diabetic neuropathy, the method comprising administering to a human in need of such treatment a therapeutically effective amount of the pharmaceutical composition of claim 87.

179. A method of activating the RET receptor in a human, the method comprising administering to the human an effective amount of the pharmaceutical composition of claim 87.

180. A method of treating a peripheral neuropathy, the method comprising administering to a human in need of such treatment a therapeutically effective amount of the pharmaceutical composition of claim 88.

181. A method of treating neuropathic pain, the method comprising administering to a human in need of such treatment a therapeutically effective amount of the pharmaceutical composition of claim 88.

182. The method of claim 181, wherein the neuropathic pain is associated with post-herpetic neuralgia.

183. The method of claim 181, wherein the neuropathic pain is associated with sciatica.

184. A method of treating painful diabetic neuropathy, the method comprising administering to a human in need of such treatment a therapeutically effective amount of the pharmaceutical composition of claim 88.

185. A method of activating the RET receptor in a human, the method comprising administering to the human an effective amount of the pharmaceutical composition of claim 88.

186. A method of treating a peripheral neuropathy, the method comprising administering to a human in need of such treatment a therapeutically effective amount of the pharmaceutical composition of claim 89.

187. A method of treating neuropathic pain, the method comprising administering to a human in need of such treatment a therapeutically effective amount of the pharmaceutical composition of claim 89.

188. The method of claim 187, wherein the neuropathic pain is associated with post-herpetic neuralgia.

189. The method of claim 187, wherein the neuropathic pain is associated with sciatica.

190. A method of treating painful diabetic neuropathy, the method comprising administering to a human in need of such treatment a therapeutically effective amount of the pharmaceutical composition of claim 89.

191. A method of activating the RET receptor in a human, the method comprising administering to the human an effective amount of the pharmaceutical composition of claim 89.

192. A nucleic acid comprising a sequence that encodes the polypeptide of claim 1.

193. An expression vector comprising the nucleic acid of claim 192.

194. A cell comprising the expression vector of claim 193.

195. A method of making a polypeptide, the method comprising:
providing the cell of claim 194, and
culturing the cell under conditions that permit expression of the nucleic acid.

196. A nucleic acid comprising a sequence that encodes the polypeptide of claim 8.

197. An expression vector comprising the nucleic acid of claim 196.

198. A cell comprising the expression vector of claim 197.

199. A method of making a polypeptide, the method comprising:
providing the cell of claim 198, and
culturing the cell under conditions that permit expression of the nucleic acid.

200. A nucleic acid comprising a sequence that encodes the polypeptide of claim 9.

201. An expression vector comprising the nucleic acid of claim 200.

202. A cell comprising the expression vector of claim 201.

203. A method of making a polypeptide, the method comprising:
providing the cell of claim 202, and
culturing the cell under conditions that permit expression of the nucleic acid.

204. A nucleic acid comprising a sequence that encodes the polypeptide of claim 10.

205. An expression vector comprising the nucleic acid of claim 204.

206. A cell comprising the expression vector of claim 205.

207. A method of making a polypeptide, the method comprising:
providing the cell of claim 206, and
culturing the cell under conditions that permit expression of the nucleic acid.

208. A nucleic acid comprising a sequence that encodes the polypeptide of claim 11.

209. An expression vector comprising the nucleic acid of claim 208.

210. A cell comprising the expression vector of claim 209.

211. A method of making a polypeptide, the method comprising:
providing the cell of claim 210, and
culturing the cell under conditions that permit expression of the nucleic acid.

212. A nucleic acid comprising a sequence that encodes the polypeptide of claim 18.

213. An expression vector comprising the nucleic acid of claim 212.

214. A cell comprising the expression vector of claim 213.

215. A method of making a polypeptide, the method comprising:
- providing the cell of claim 214, and
- culturing the cell under conditions that permit expression of the nucleic acid.

216. A nucleic acid comprising a sequence that encodes the polypeptide of claim 19.

217. An expression vector comprising the nucleic acid of claim 216.

218. A cell comprising the expression vector of claim 217.

219. A method of making a polypeptide, the method comprising:
- providing the cell of claim 218, and
- culturing the cell under conditions that permit expression of the nucleic acid.

* * * * *

UNITED STATES PATENT AND TRADEMARK OFFICE
CERTIFICATE OF CORRECTION

PATENT NO. : 8,263,553 B2
APPLICATION NO. : 11/573773
DATED : September 11, 2012
INVENTOR(S) : Anthony Rossomando, Laura Silvian and R. Blake Pepinsky It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1441 days.

On the Title page,

Item [57], ABSTRACT, delete "Compositions and methods for folding proteins belonging to the transforming growth factor beta superfamily are disclosed. The compositions and methods allow for the folding of such proteins when produced in an expression system that does not yield a properly folded, biologically active product."
and insert -- Variant Neublastin polypeptides having substitutions at selected amino acid residues are disclosed. Substitution at one or more selected amino acid residues decreases heparin binding and increases serum exposure of variant Neublastin polypeptides. Also disclosed are methods of using variant Neublastin polypeptides to treat disorders and activate the RET receptor in a mammal. --.

Signed and Sealed this
Twenty-third Day of July, 2013

Teresa Stanek Rea
*Acting Director of the United States Patent and Trademark Office*